US007560455B2

(12) United States Patent
Biftu et al.

(10) Patent No.: US 7,560,455 B2
(45) Date of Patent: Jul. 14, 2009

(54) 3-AMINO-4-PHENYLBUTANOIC ACID DERIVATIVES AS DIPEPTIDYL PEPTIDASE INHIBITORS FOR THE TREATMENT OR PREVENTION OF DIABETES

(75) Inventors: Tesfaye Biftu, Freehold, NJ (US); Danqing Dennis Feng, Branchburg, NJ (US); Gui Bai Liang, Scotch Plains, NJ (US); Xiaoxia Qian, New York, NY (US)

(73) Assignee: Merck & Co., Inc., Rahway, NJ (US)

( * ) Notice: Subject to any disclaimer, the term of this patent is extended or adjusted under 35 U.S.C. 154(b) by 611 days.

(21) Appl. No.: 10/556,805

(22) PCT Filed: May 10, 2004

(86) PCT No.: PCT/US2004/014642

§ 371 (c)(1),
(2), (4) Date: Nov. 14, 2005

(87) PCT Pub. No.: WO2004/103276

PCT Pub. Date: Dec. 2, 2004

(65) Prior Publication Data

US 2006/0258646 A1 Nov. 16, 2006

Related U.S. Application Data

(60) Provisional application No. 60/470,564, filed on May 14, 2003.

(51) Int. Cl.
*A61P 3/10* (2006.01)
*A61K 31/55* (2006.01)
*C07D 491/00* (2006.01)

(52) U.S. Cl. .................... 514/221; 540/568
(58) Field of Classification Search .......... 514/221; 540/568

See application file for complete search history.

(56) References Cited

U.S. PATENT DOCUMENTS

| 4,386,090 A | 5/1983 | Moinet et al. |
| 5,939,560 A | 8/1999 | Jenkins et al. |
| 6,011,155 A | 1/2000 | Villhauer |
| 6,166,063 A | 12/2000 | Villhauer |
| 6,303,661 B1 | 10/2001 | Demuth et al. |
| 6,432,969 B1 | 8/2002 | Villhauer |
| 6,699,871 B2 | 3/2004 | Edmondson et al. |

FOREIGN PATENT DOCUMENTS

| WO | WO 97/40832 | 11/1997 |
| WO | WO 98/19998 A2 | 5/1998 |
| WO | WO 00/34241 | 6/2000 |
| WO | WO 01/34594 A1 | 5/2001 |
| WO | WO 01/42262 | 6/2001 |
| WO | WO 01/96295 A2 | 12/2001 |
| WO | WO 02/02560 A2 | 1/2002 |
| WO | WO 02/076450 A1 | 10/2002 |
| WO | WO 03/000180 A2 | 1/2003 |
| WO | WO 03/000181 A2 | 1/2003 |
| WO | WO 03/002530 A2 | 1/2003 |
| WO | WO 03/082817 A2 | 10/2003 |
| WO | WO 2004/007468 A1 | 1/2004 |
| WO | WO 2004/032836 A2 | 4/2004 |
| WO | WO 2004/043940 | 5/2004 |
| WO | WO 2004/050022 A2 | 6/2004 |
| WO | WO 2004/058266 A1 | 7/2004 |
| WO | WO 2004/064778 A2 | 8/2004 |
| WO | WO 2004/069162 A2 | 8/2004 |
| WO | WO 2004/110436 | 12/2004 |
| WO | WO 2004/112701 A2 | 12/2004 |
| WO | WO 2005/011581 A2 | 2/2005 |
| WO | WO 2005/044195 A2 | 5/2005 |
| WO | WO 2005/056003 A1 | 6/2005 |
| WO | WO 2005/056013 A1 | 6/2005 |
| WO | WO 2005/108382 A1 | 11/2005 |
| WO | WO 2005/116029 A1 | 12/2005 |
| WO | WO 2005/123685 A1 | 12/2005 |

OTHER PUBLICATIONS

J. J. Holst, "Treatment of Type 2 Diabetes Mellitus with Agonists of the GLP-1 Receptor or DPP-IV Inhibitors", Expert Opin. Emerg. Drugs, vol. 9(1) pp. 155-166(2004).

C. F. Deacon, et al., "Inhibitors of dipeptidyl peptidase IV: A Novel Approach for the Prevention and Treatment of Type 2 Diabetes?", Expert Opin. Investig. Drugs, vol. 13(9) pp. 1091-1102(2004).

K. Augustyns et al., "Dipeptidyl Peptidase IV Inhibitors as New Therapeutic Agents for the Treatment of Type 2 Diabetes", Expert Opin. Ther. Patents, vol. 13(4), pp. 499-510(2003).

Novartis AG: WO0034241, "Novel N-substituted-2-Cyanopyrolidines as Potent Inhibitors of Dipeptidyl Peptidase IV in the Treatment of Non-Insulin-Dependent Diabetes Mellitus", Exp. Opin. Ther. Patents, vol. 10(12), pp. 1937-1942 (2000).

T. P. Vahl & D. A. D'Alessio, "Gut peptides in the treatment of diabetes mellitus" Exp. Opin. Invest. Drugs, vol. 13, pp. 177-188 (2004).

L. B. Knudsen, "Glucagon-like peptide-1: The Basis of a New Class of Treatment for Type 2 Diabetes", J. Med. Chem, vol. 47, pp. 4128-4134 (2004).

(Continued)

*Primary Examiner*—Brenda L Coleman
(74) *Attorney, Agent, or Firm*—Philippe L. Durette; Catherine D. Fitch

(57) ABSTRACT

The pre-sent invention is directed to 3-amino-4-phenylbutanoic acid derivatives which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

24 Claims, No Drawings

OTHER PUBLICATIONS

A. E. Weber, "Dipeptidyl Peptidase IV Inhibitors for the Treatment of Diabetes", J. Med. Chem, vol. 47, pp. 4135-4141 (2004).

J. J. Holst and C. F. Deacon, "Glucagon-like peptide 1 and inhibitors of dipeptidyl peptidase IV in the treatment of type 2 diabetes mellitus", Curr. Opin Pharmacology, vol. 4, pp. 589-596 (2004).

C. F. Deacon, "Perspectives in Diabetes—Therapeutic Strategies Based on Glucagon-Like Peptide 1", Diabetes, vol. 53, pp. 2181-2189 (2004).

K. Augustyns, et al., "Inhibitors of proline-specific dipeptidyl peptidase: DPP IV inhibitors as a novel approach for the treatment of Type 2 diabetes", Expert Opin. Ther. Patents, vol. 15(10), pp. 1387-1407 (2005).

Hans-Ulrich Demuth, et al., "Type 2 diabetes—Therapy with dipeptidyl peptidase IV inhibitors", Biochimica et Biophysica Acta, vol. 1751, pp. 33-44 (2005).

Drucker, D. J., "Therapeutic potential of dipeptidyl peptidase IV inhibitors for the treatment of type 2 diabetes" Expert Opin. Investig. Drugs, vol. 12, No. 1, pp. 87-100, 2003.

3-AMINO-4-PHENYLBUTANOIC ACID DERIVATIVES AS DIPEPTIDYL PEPTIDASE INHIBITORS FOR THE TREATMENT OR PREVENTION OF DIABETES

CROSS REFERENCE TO RELATED APPLICATIONS

This application is the National Stage of International Application No. PCT/US04/014642, filed 10 May 2004, which claims the benefit under 35 U.S.C. 119(e) of U.S. Provisional Application No. 60/470,564 filed 14 May 2003.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DP-IV" or "DPP-IV") enzyme are also under investigation as drugs that may be useful in the treatment of diabetes, and particularly type 2 diabetes. See for example WO 97/40832, WO 98/19998, U.S. Pat. No. 5,939,560, *Bioorg. Med. Chem. Lett.*, 6: 1163-1166 (1996); and *Bioorg. Med. Chem. Lett.*, 6: 2745-2748 (1996). The usefulness of DP-IV inhibitors in the treatment of type 2 diabetes is based on the fact that DP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DP-IV leads to decreased inactivation of the incretins, and this in turn results in increased effectiveness of the incretins in stimulating production of insulin by the pancreas. DP-IV inhibition therefore results in an increased level of serum insulin. Advantageously, since the incretins are produced by the body only when food is consumed, DP-IV inhibition is not expected to increase the level of insulin at inappropriate times, such as between meals, which can lead to excessively low blood sugar (hypoglycemia). Inhibition of DP-IV is therefore expected to increase insulin without increasing the risk of hypoglycemia, which is a dangerous side effect associated with the use of insulin secretagogues.

DP-IV inhibitors also have other therapeutic utilities, as discussed herein. DP-TV inhibitors have not been studied extensively to date, especially for utilities other than diabetes. New compounds are needed so that improved DP-IV inhibitors can be found for the treatment of diabetes and potentially other diseases and conditions. The therapeutic potential of DP-IV inhibitors for the treatment of type 2 diabetes is discussed by D. J. Drucker in *Exp. Opin. Invest. Drugs*, Vol. 12, No. 1, pp. 87-100 (2003).

SUMMARY OF THE INVENTION

The present invention is directed to 3-amino-4-phenylbutanoic acid derivatives which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention relates to 3-amino-4-phenylbutanoic acid derivatives useful as inhibitors of dipeptidyl peptidase-IV. Compounds of the present invention are described by structural formula I:

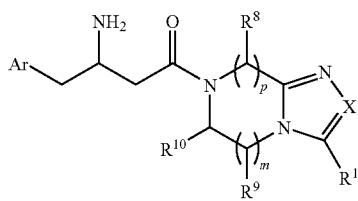

(I)

wherein
each n is independently 0, 1, or 2;
m is 1 or 2;
p is 1 or 2; with the proviso that m+p is 3;
X is N or $CR^2$;
Ar is phenyl substituted with one to five $R^3$ substituents;
$R^1$ and $R^2$ are each independently selected from the group consisting of
  hydrogen,
  halogen,
  hydroxy,
  cyano,
  $C_{1-10}$ alkyl, wherein alkyl is unsubstituted or substituted with one to five substituents independently selected from halogen or hydroxy,
  $C_{1-10}$ alkoxy, wherein alkoxy is unsubstituted or substituted with one to five substituents independently selected from halogen or hydroxy,
  $C_{1-10}$ alkylthio, wherein alkylthio is unsubstituted or substituted with one to five substituents independently selected from halogen or hydroxy,
  $C_{2-10}$ alkenyl, wherein alkenyl is unsubstituted or substituted with one to five substituents independently selected from halogen or hydroxy,
  $(CH_2)_n$COOH,
  $(CH_2)_n$COOC$_{1-6}$ alkyl,
  $(CH_2)_n$CONR$^4$R$^5$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens; or $R^4$ and $R^5$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
  $(CH_2)_n$—NR$^4$R$^5$,
  $(CH_2)_n$—OCONR$^4$R$^5$,
  $(CH_2)_n$—SO$_2$NR$^4$R$^5$,
  $(CH_2)_n$—SO$_2$R$^6$,
  $(CH_2)_n$—NR$^7$SO$_2$R$^6$,
  $(CH_2)_n$—NR$^7$CONR$^4$R$^5$,
  $(CH_2)_n$—NR$^7$COR$^7$,
  $(CH_2)_n$—NR$^7$CO$_2$R$^6$,
  $(CH_2)_n$—COR$^6$,
  $(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens,
  $(CH_2)_n$-aryl, wherein aryl is unsubstituted or substituted with one to five substituents independently selected from halogen, cyano, hydroxy, NR$^7$SO$_2$R$^6$, SO$_2$R$^6$, CO$_2$H, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, and
  $(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens,
  wherein any methylene ($CH_2$) carbon atom in $R^1$ or $R^2$ is unsubstituted or substituted with one to two groups independently selected from halogen, hydroxy, and $C_{1-4}$ alkyl unsubstituted or substituted with one to five halogens;
each $R^3$ is independently selected from the group consisting of
  hydrogen,
  halogen,
  cyano,
  hydroxy,
  $C_{1-6}$ alkyl, unsubstituted or substituted with one to five halogens, and
  $C_{1-6}$ alkoxy, unsubstituted or substituted with one to five halogens;
$R^6$ is independently selected from the group consisting of tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, and wherein any methylene ($CH_2$) carbon atom in $R^6$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;

each $R^7$ is hydrogen or $R^6$;

each $R^8$, $R^9$, and $R^{10}$ is independently selected from the group consisting of hydrogen, cyano, carboxy, $C_{1-6}$ alkyloxycarbonyl, $C_{1-10}$ alkyl, unsubstituted or substituted with one to five substituents independently selected from halogen, hydroxy, $C_{1-6}$ alkoxy, carboxy, $C_{1-6}$ alkyloxycarbonyl, and phenyl-$C_{1-3}$ alkoxy, wherein alkoxy is unsubstituted or substituted with one to five halogens, $(CH_2)_n$-aryl, wherein aryl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, $(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens, $(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens, and $(CH_2)_n CONR^4R^5$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens; or $R^4$ and $R^5$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

wherein any methylene ($CH_2$) carbon atom in $R^8$, $R^9$ or $R^{10}$ is unsubstituted or substituted with one to two groups independently selected from halogen, hydroxy, and $C_{1-4}$ alkyl unsubstituted or substituted with one to five halogens.

In one embodiment of the compounds of the present invention, the carbon atom marked with an * has the R configuration as depicted in formula Ia

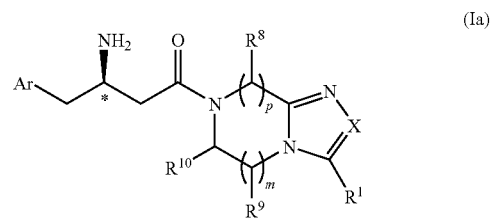

(Ia)

wherein Ar, X, $R^1$, $R^8$, $R^9$, $R^{10}$, m and p are as defined herein.

In a second embodiment of the compounds of the present invention, p is 1 and m is 2 as depicted in formula Ib:

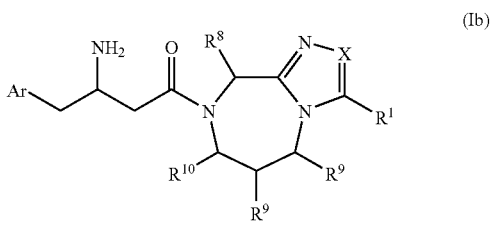

(Ib)

wherein Ar, X, $R^1$, $R^8$, $R^9$, and $R^{10}$ are as defined herein.

In a class of this second embodiment, the carbon atom marked with an * has the R configuration as depicted in formula Ic:

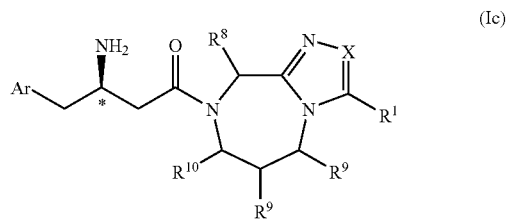

(Ic)

wherein Ar, X, $R^1$, $R^8$, $R^9$, and $R^{10}$ are as defined herein.

In another class of this second embodiment, X is N as depicted in formula Id:

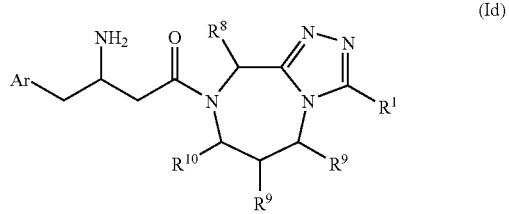

(Id)

wherein Ar, $R^1$, $R^8$, $R^9$, and $R^{10}$ are as defined herein.

In a third class of this second embodiment, X is CR² as depicted in formula Ie:

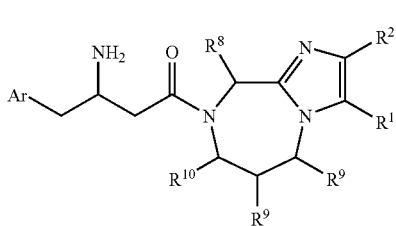

(Ie)

wherein Ar, R¹, R², R⁸, R⁹, and R¹⁰ are as defined herein.

In third embodiment of the compounds of the present invention, p is 2 and m is 1 as depicted in formula If:

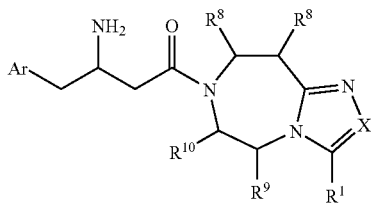

(If)

wherein Ar, X, R¹, R⁸, R⁹, and R¹⁰ are as defined herein.

In a class of this third embodiment, the carbon atom marked with an * has the R configuration as depicted in formula Ig:

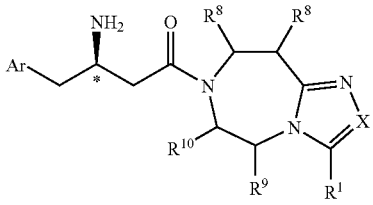

(Ig)

wherein Ar, X, R¹, R⁸, R⁹, and R¹⁰ are as defined herein.

In another class of this third embodiment of the compounds of the present invention, X is N as depicted in formula Ih:

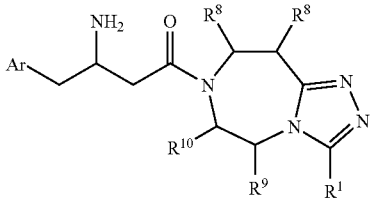

(Ih)

wherein Ar, R¹, R⁸, R⁹, and R¹⁰ are as defined herein.

In a third class of this third embodiment of the compounds of the present invention, X is CR2 as depicted in formula Ii:

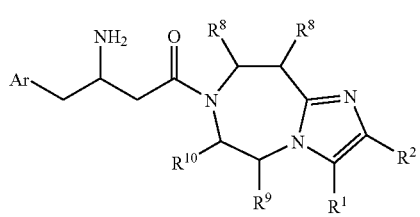

(Ii)

wherein Ar, R¹, R², R⁸, R⁹, and R¹⁰ are as defined herein.

In a fourth embodiment of the compounds of the present invention, R³ is selected from the group consisting of hydrogen, fluoro, chloro, bromo, trifluoromethyl, and methyl. In a class of this embodiment, R³ is selected from the group consisting of hydrogen, fluoro, and chloro. In a subclass of this class, R³ is hydrogen or fluoro.

In a fifth embodiment of the compounds of the present invention, R¹ is selected from the group consisting of:
  hydrogen,
  halogen,
  $C_{1-6}$ alkyl, wherein alkyl is unsubstituted or substituted with one to five substituents independently selected from halogen or hydroxy,
  $(CH_2)_n$-aryl, wherein aryl is unsubstituted or substituted with one to five substituents independently selected from halogen, CN, hydroxy, $NR^7SO_2R^6$, $SO_2R^6$, $CO_2H$, $C_{1-6}$ alkyloxycarbonyl, $C_{1-6}$ alkyl, and
  $C_{1-6}$ alkoxy, wherein alkyl and alkoxy are unsubstituted or substituted with one to five halogens;
  $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, and
  wherein any methylene ($CH_2$) carbon atom in R¹ is unsubstituted or substituted with one to two groups independently selected from halogen, hydroxy, and $C_{1-4}$ alkyl unsubstituted or substituted with one to five halogens.

In a class of this embodiment of the compounds of the present invention, R¹ is selected from the group consisting of
  hydrogen,
  methyl,
  trifluoromethyl,
  phenyl,
  4-fluorophenyl,
  4-trifluoromethyl)phenyl,
  4-(trifluoromethoxy)phenyl, and
  5-methyl-1,3,4-oxadiazol-2-yl.

In a sixth embodiment of the compounds of the present invention, R² is selected from the group consisting of
  hydrogen,
  halogen, and
  $C_{1-6}$ alkyl, wherein alkyl is unsubstituted or substituted with one to five substituents independently selected from halogen or hydroxy.

In a class of this embodiment of the compounds of the present invention, R² is selected from the group consisting of:
  hydrogen, and
  trifluoromethyl.

In a seventh embodiment of the compounds of the present invention, $R^8$, $R^9$, and $R^{10}$ are independently selected from the group consisting of:

hydrogen, and $C_{1-6}$ alkyl, unsubstituted or substituted with one to five substituents independently selected from halogen, hydroxy, $C_{1-6}$ alkoxy, and phenyl-$C_{1-3}$ alkoxy, wherein alkoxy is unsubstituted or substituted with one to five halogens.

In a class of this embodiment of the compounds of the present invention, $R^8$, $R^9$, and $R^{10}$ are each independently selected from the group consisting of hydrogen and methyl.

In a subclass of this class, $R^9$ and $R^{10}$ are hydrogen.

Illustrative, but nonlimiting, examples of compounds of the present invention that are useful as dipeptidyl peptidase-IV inhibitors are the following:

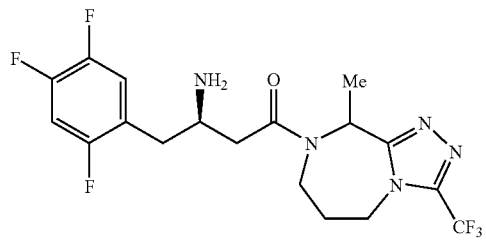

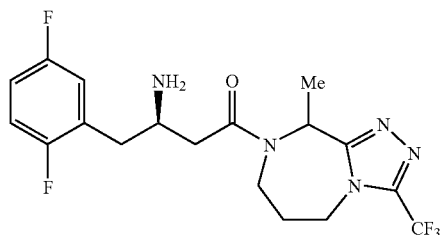

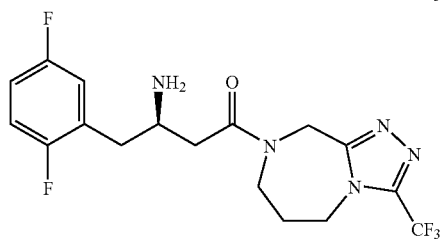

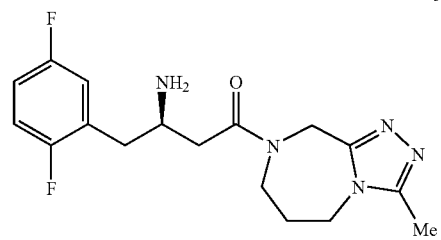

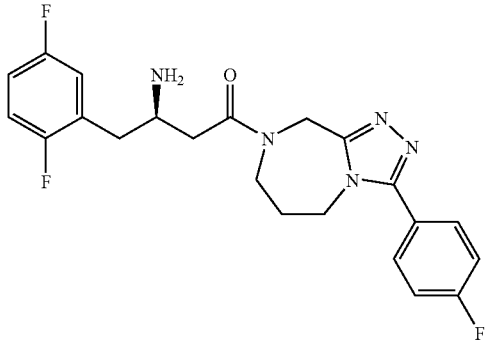

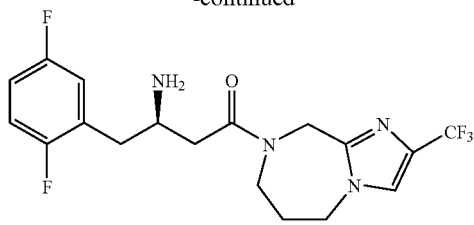

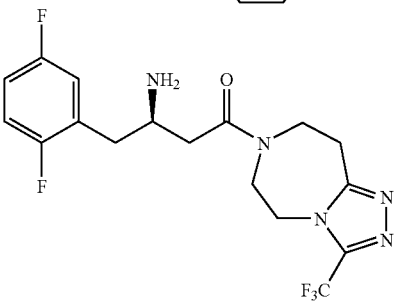

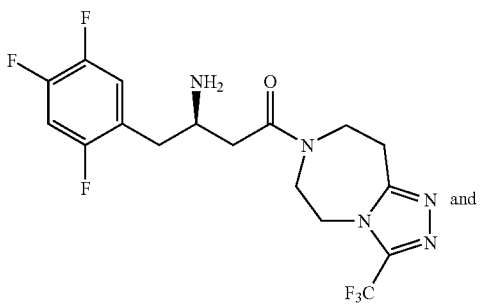

or a pharmaceutically acceptable salt thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-10}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-10}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Heterocycle" and "heterocyclyl" refer to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

"Heteroaryl" means an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-1H)-pyridinyl (2-hydroxy-pyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-a]pyridinyl, [1,2,4-triazolo][4,3-a]pyridinyl, pyrazolo[1,5-a]pyridinyl, [1,2,4-triazolo][1,5-a]pyridinyl, 2-oxo-1,3-benzoxazolyl, 4-oxo-3H-quinazolinyl, 3-oxo[1,2,4]-triazolo[4,3-a]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The compounds of the present invention may contain one or more asymmetric centers and can thus occur as racemates and racemic mixtures, single enantiomers, diastereomeric mixtures and individual diastereomers. The compounds of the present invention have one asymmetric center at the carbon atom marked with an * in formula Ia. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formula Ia shows the preferred sterochemistry at the carbon atom to which is attached the amino group of the beta amino acid from which these compounds are prepared.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Solvates, and in particular, the hydrates of the compounds of structural formula I are included in the present invention as well.

Exemplifying the invention is the use of the compounds disclosed in the Examples and herein.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutically acceptable carrier or diluent.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DP-IV to release the fluorescent AMC leaving group. The kinetic parameters that describe this reaction are as follows: $K_m=50$ μM; $k_{cat}=75 \text{ s}^{-1}$; $k_{cat}/K_m=1.5\times10^6 \text{ M}^{-1}\text{s}^{-1}$. A typical reaction contains approximately 50 pM enzyme, 50 μM Gly-Pro-AMC, and buffer (100 mM HEPES, pH 7.5, 0.1 mg/ml BSA) in a total reaction volume of 100 μl. Liberation of AMC is monitored continuously in a 96-well plate fluorometer using an excitation wavelength of 360 nm and an emission wavelength of 460 nm. Under these conditions, approximately 0.8 μM AMC is produced in 30 minutes at 25 degrees C. The enzyme used in these studies was soluble (transmembrane domain and cytoplasmic extension excluded) human-protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an $IC_{50}$ of less than about 1 µM. Such a result is indicative of the intrinsic activity of the compounds in use as inhibitors the dipeptidyl peptidase-IV enzyme activity.

Dipeptidyl peptidase-IV enzyme (DP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DP-IV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions.

Type II Diabetes and Related Disorders: It is well established that the incretins GLP-1 and GIP are rapidly inactivated in vivo by DP-IV. Studies with DP-IV$^{(-/-)}$-deficient mice and preliminary clinical trials indicate that DP-TV inhibition increases the steady state concentrations of GLP-1 and GIP, resulting in improved glucose tolerance. By analogy to GLP-1 and GIP, it is likely that other glucagon family peptides involved in glucose regulation are also inactivated by DP-IV (eg. PACAP). Inactivation of these peptides by DP-IV may also play a role in glucose homeostasis. The DP-IV inhibitors of the present invention therefore have utility in the treatment of type II diabetes and in the treatment and prevention of the numerous conditions that often accompany Type II diabetes, including metabolic syndrome X, reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

Obesity: DP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.*, 277: R910-R916 (1999)). ICV administration of GLP-1 in rats and mice also has profound effects on food intake (*Nature Medicine.* 2: 1254-1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DP-IV. ICV administration of GLP-2 also inhibits food intake, analogous to the effects observed with GLP-1 (*Nature Medicine.* 6: 802-807 (2000)). In addition, studies with DP-IV deficient mice suggest that these animals are resistant to diet-induced obesity and associated pathology (e.g. hyperinsulinonemia).

Growth Hormone Deficiency: DP-W inhibition may be useful for the treatment of growth hormone deficiency, based on the hypothesis that growth-hormone releasing factor (GRF), a peptide that stimulates release of growth hormone from the anterior pituitary, is cleaved by the DP-IV enzyme in vivo (WO 00/56297). The following data provide evidence that GRF is an endogenous substrate: (1) GRF is efficiently cleaved in vitro to generate the inactive product GRF[3-44] (*BBA* 1122: 147-153 (1992)); (2) GRF is rapidly degraded in plasma to GRF[3-44]; this is prevented by the DP-IV inhibitor diprotin A; and (3) GRF[3-44] is found in the plasma of a human GRF transgenic pig (*J. Clin. Invest.*, 83: 1533-1540 (1989)). Thus DP-IV inhibitors may be useful for the same spectrum of indications which have been considered for growth hormone secretagogues.

Intestinal Injury: The potential for using DP-IV inhibitors for the treatment of intestinal injury is suggested by the results of studies indicating that glucagon-like peptide-2 (GLP-2), a likely endogenous substrate for DP-IV, may exhibit trophic effects on the intestinal epithelium (*Regulatory Peptides.* 90: 27-32 (2000)). Administration of GLP-2 results in increased small bowel mass in rodents and attenuates intestinal injury in rodent models of colitis and enteritis.

Immunosuppression: DP-IV inhibition may be useful for modulation of the immune response, based upon studies implicating the DP-IV enzyme in T cell activation and in chemokine processing, and efficacy of DP-IV inhibitors in in vivo models of disease. DP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DP-IV hydrolysis.

DP-IV inhibitors have been shown to be efficacious immunosupressants in animal models of transplantation and arthritis. Prodipine (Pro-Pro-diphenyl-phosphonate), an irreversible inhibitor of DP-IV, was shown to double cardiac allograft survival in rats from day 7 to day 14 (*Transplantation,* 63: 1495-1500 (1997)). DP-IV inhibitors have been tested in collagen and alkyldiamine-induced arthritis in rats and showed a statistically significant attenuation of hind paw swelling in this model [*Int. J. Immunopharmacology,* 19:15-24 (1997) and *Immunopharmacology,* 40: 21-26 (1998)]. DP-IV is upregulated in a number of autoimmune diseases including rheumatoid arthritis, multiple sclerosis, Graves' disease, and Hashimoto's thyroiditis (*Immunology Today,* 20: 367-375 (1999)).

HIV Infection: DP-IV inhibition may be useful for the treatment or prevention of HIV infection or AIDS because a number of chemokines which inhibit HIV cell entry are potential substrates for DP-IV (*Immunology Today* 20: 367-375 (1999)). In the case of SDF-1alpha, cleavage decreases antiviral activity (*PNAS*, 95: 6331-6 (1998)). Thus, stabilization of SDF-1alpha through inhibition of DP-IV would be expected to decrease HIV infectivity.

Hematopoiesis: DP-IV inhibition may be useful for the treatment or prevention of hematopiesis because DP-IV may be involved in hematopoiesis. A DP-IV inhibitor, Val-Boro-Pro, stimulated hematopoiesis in a mouse model of cyclophosphamide-induced neutropenia (WO 99/56753).

Neuronal Disorders: DP-IV inhibition may be useful for the treatment or prevention of various neuronal or psychiatric disorders because a number of peptides implicated in a variety of neuronal processes are cleaved in vitro by DP-IV. A DP-IV inhibitor thus may have a therapeutic benefit in the treatment of neuronal disorders. Endomorphin-2, beta-casomorphin, and substance P have all been shown to be in vitro substrates for DP-IV. In all cases, in vitro cleavage is highly efficient, with $k_{cat}/K_m$ about $10^6$ $M^{-1}s^{-1}$ or greater. In an electric shock jump test model of analgesia in rats, a DP-IV inhibitor showed a significant effect that was independent of the presence of exogenous endomorphin-2 (*Brain Research*, 815: 278-286 (1999)).

Neuroprotective and neuroregenerative effects of DP-IV inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl Peptidase-IV In Vitro and In Vivo," *Int. Conf. On Dipeptidyl Aminopeptidases: Basic Science and Clinical Applications*. Sep. 26-29, 2002 (Berlin, Germany)].

Tumor Invasion and Metastasis: DP-IV inhibition may be useful for the treatment or prevention of tumor invasion and metastasis because an increase or decrease in expression of several ectopeptidases including DP-IV has been observed during the transformation of normal cells to a malignant phenotype (*J. Exp. Med.*, 190: 301-305 (1999)). Up- or down-regulation of these proteins appears to be tissue and cell-type specific. For example, increased CD26/DP-IV expression has been observed on T cell lymphoma, T cell acute lymphoblastic leukemia, cell-derived thyroid carcinomas, basal cell carcinomas, and breast carcinomas. Thus, DP-IV inhibitors may have utility in the treatment of such carcinomas.

Benign Prostatic Hypertrophy: DP-IV inhibition may be useful for the treatment of benign prostatic hypertrophy because increased DP-IV activity was noted in prostate tissue from patients with BPH (*Eur. J. Clin. Chem. Clin. Biochem.*, 30: 333-338 (1992)).

Sperm motility/male contraception: DP-IV inhibition may be useful for the altering sperm motility and for male contraception because in seminal fluid, prostatosomes, prostate derived organelles important for sperm motility, possess very high levels of DP-IV activity (*Eur. J. Clin. Chem. Clin. Biochem.*, 30: 333-338 (1992)).

Gingivitis: DP-IV inhibition may be useful for the treatment of gingivitis because DP-IV activity was found in gingival crevicular fluid and in some studies correlated with periodontal disease severity (*Arch. Oral Biol.*, 37: 167-173 (1992)).

Osteoporosis: DP-IV inhibition may be useful for the treatment or prevention of osteoporosis because GIP receptors are present in osteoblasts.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type II diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated or prevented by inhibition of DP-IV.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DP-IV) inhibitors;

(b) insulin sensitizers including (i) PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as fenofibric acid derivatives (gemfibrozil, clofibrate, fenofibrate and bezafibrate), (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide glyburide, glipizide, glimepiride, and meglitinides, such as repaglinide;

(e) α-glucosidase inhibitors (such as acarbose and miglitol);

(f) glucagon receptor antagonists such as those disclosed in WO 98/04528, WO 99/01423, WO 00/39088, and WO 00/69810;

(g) GLP-1, GLP-1 mimetics, and GLP-1 receptor agonists such as those disclosed in WO00/42026 and WO00/59887;

(h) GIP and GIP mimetics such as those disclosed in WO00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as KRP-297, (vi) inhibitors of cholesterol absorption, such as beta-sitosterol and ezetimibe, (vii) acyl CoA:cholesterol acyltransferase inhibitors, such as avasimibe, and (viii) anti-oxidants, such as probucol;

(k) PPARδ agonists, such as those disclosed in WO97/28149;

(l) antiobesity compounds such as fenfluramine, dexfenfluramine, phentermine, sibutramine, orlistat, neuropeptide Y5 inhibitors, cannabinoid-1 (CB-1) receptor antagonists/inverse agonists, melanocortin-4 receptor agonists, and $\beta_3$ adrenergic receptor agonists;

(m) ileal bile acid transporter inhibitors;

(n) agents intended for use in inflammatory conditions such as aspirin, non-steroidal anti-inflammatory drugs, glucocorticoids, azulfidine, and selective cyclooxygenase-2 inhibitors; and (o) antihypertensive agents such as ACE inhibitors (enalapril, lisinopril, captopril, quinapril, tandolapril), A-II receptor blockers (losartan, candesartan, irbesartan, valsartan, telmisartan, eprosartan), beta blockers and calcium channel blockers.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, PPAR agonists, PTP-1B inhibitors, other DP-IV inhibitors, and anti-obesity compounds.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay, disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of The present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared from beta amino acid intermediates such as those of formula II and substituted fused tetrahydrodiazepine intermediates such as those of formula m, using standard peptide coupling conditions followed by deprotection. The preparation of these intermediates is described in the following Schemes.

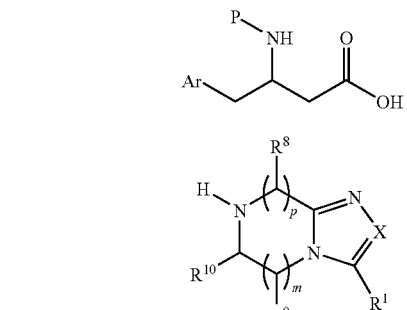

wherein Ar, X, $R^1$, $R^8$, $R^9$, $R^{10}$, m and p are as defined above and P is a suitable nitrogen protecting group such as tert-butoxycarbonyl (BOC), benzyloxycarbonyl (Cbz), and 9-fluorenylmethoxycarbonyl (Fmoc).

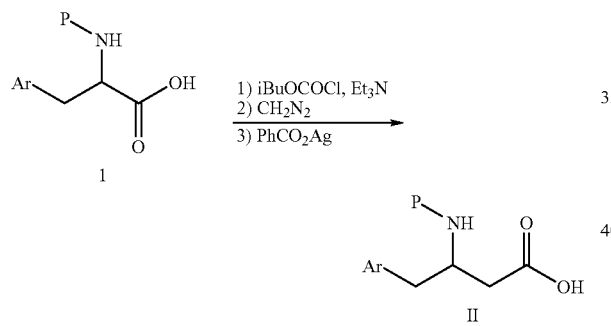

Compounds of formula II are commercially available, known in the literature or may be conveniently prepared by a variety of methods familiar to those skilled in the art. One common route is illustrated in Scheme 1. Protected alpha-amino acid 1, which may be commercially available or readily prepared from the corresponding amino acid by protection using, for example, di-tert-butyl dicarbonate (for P=BOC), carbobenzyloxy chloride (for P=Cbz), or N-(9-fluorenylmethoxy-carbonyloxy)succinimide (for P=Fmoc), is treated with isobutyl chloroformate and a base such as triethylamine or diisopropylethylamine, followed by diazomethane. The resultant diazoketone is then treated with silver benzoate in a solvent such as methanol or aqueous dioxane and may be subjected to sonication following the procedure of Sewald et al., *Synthesis,* 837 (1997) in order to provide the beta amino acid II. As will be understood by those skilled in the art, for the preparation of enantiomerically pure beta amino acids II, enantiomerically pure alpha amino acids 1 may be used. Alternate routes to the protected beta-amino acid intermediates II can be found in the following reviews: E. Juaristi, *Enantioselective Synthesis of β-Amino Acids,* Ed., Wiley-VCH, New York: 1997; Juaristi et al., *Aldrichimica Acta.* 27: 3 (1994); and Cole et al., *Tetrahedron.* 32: 9517 (1994).

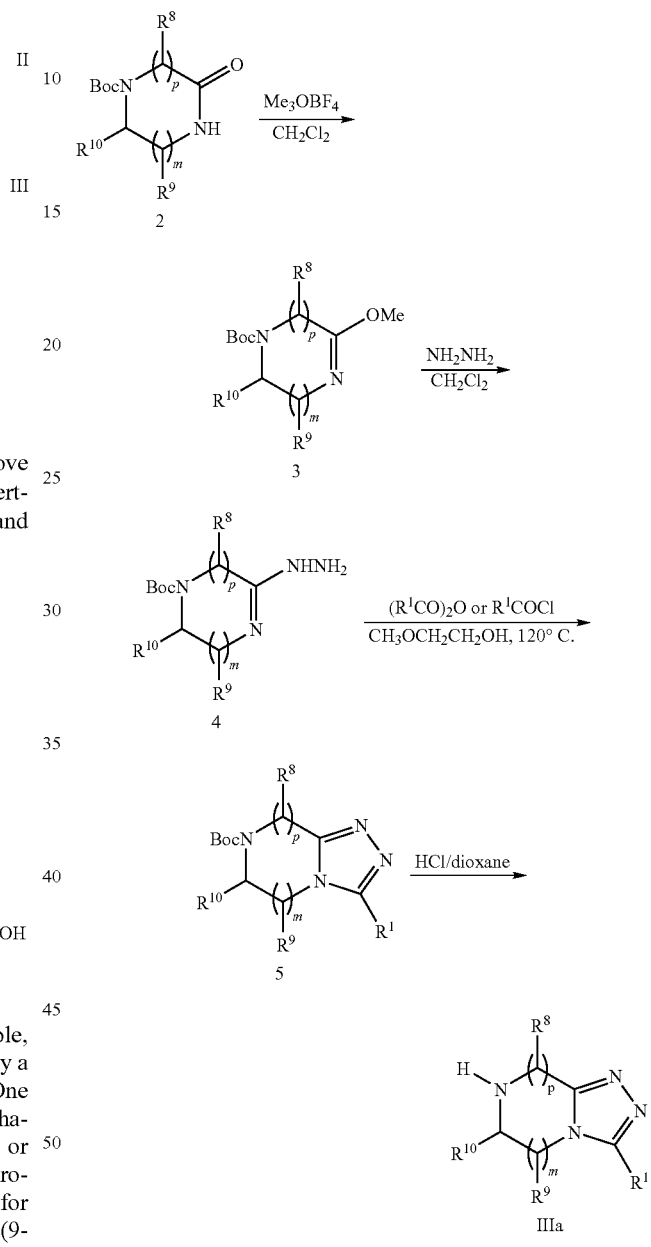

Compounds of formual IIIa wherein X is N, may be prepared as illustrated in Scheme 2. The appropriately substituted compound 2 is treated with trimethyloxonium tetrafluoroborate to form the corresponding methoxyimine 3. Treatment with hydrazine in solvents such as dichloromethane provides intermediate 4. Acylation with an anhydride or acid chloride followed by heating, for example in methoxyethanol, gives the cyclized derivative 5. Deprotection, in the case of Boc under acidic conditions, conveniently hydrogen chloride in dioxane, provides the desired intermediate IIIa.

SCHEME 3

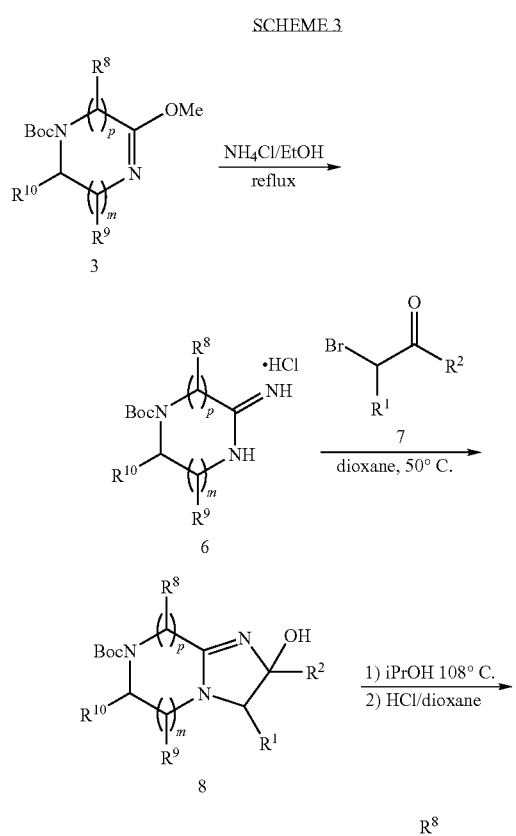

Intermediates IIIb, wherein X is CR², may be prepared as illustrated in Scheme 3. Methoxyimine 3, prepared as described in Scheme 2, is treated with ammonium chloride in a solvent such as ethanol at elevated temperatures to give amidine 6. Condensation with an appropriately substituted bromoketone 7, by heating in dioxane to give intermediate 8, followed by dehydration, conveniently by heating in isopropanol, provides, after removal of the Boc protecting group, the desired intermediate IIIb.

SCHEME 4

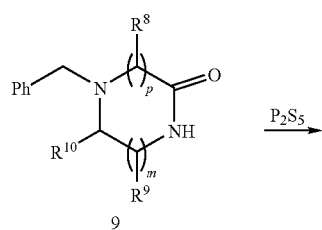

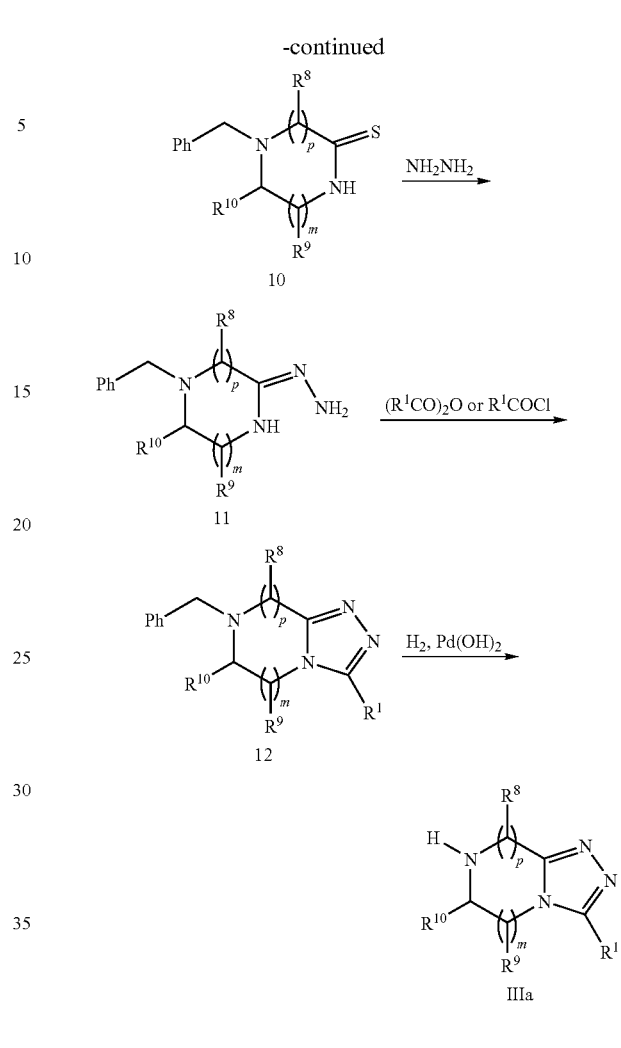

An alternate route to intermediate IIIa is shown in Scheme 4. N-benzyl protected heterocycle 9 is converted to thiolactam 10 with phosphorus pentasulfide or other thiating reagents such as Lawesson's reagent Treatment with hydrazine provides the hydrazone 11. Cyclization of the hydrazone to triazolo 12 is carried out as described above for Scheme 2. Deprotection under catalytic hydrogenation conditions provides intermediate IIIa.

Starting material 9 is commercially available, known in the literature, or may be conveniently prepared by a variety of methods commonly known to those skilled in the art. It is readily available from intermediate 2 by manipulation of protecting groups, for example, by treatment of 2 with acid to remove the Boc group, and then alkylation with benzyl bromide to install the N-benzyl group.

SCHEME 5

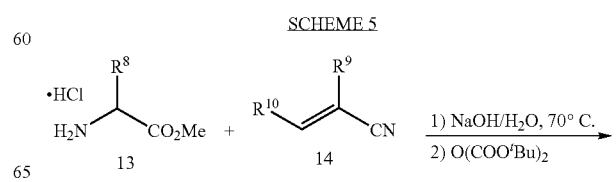

-continued

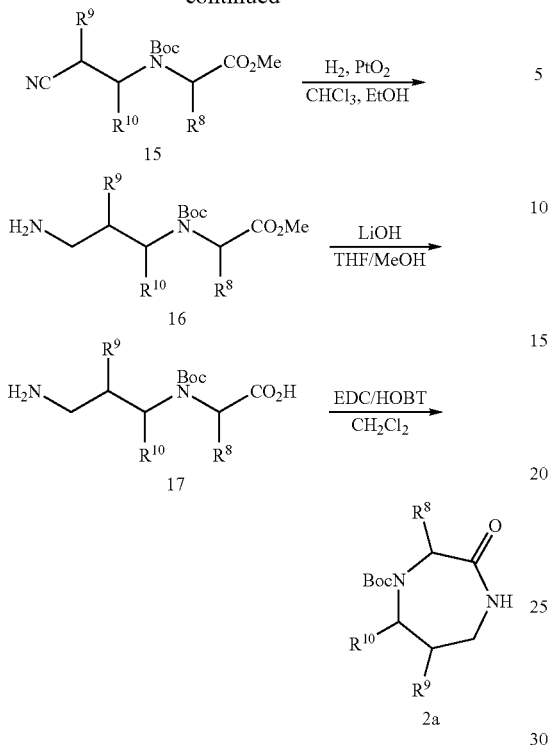

Starting material 2 is commercially available, known in the literature, or may be conveniently prepared by a variety of methods commonly known to those skilled in the art. One convenient method to prepare compound 2a wherein $R^9$ adjacent to the amide is hydrogen, p is 1 and m is 2, is shown in Scheme 5. Amino ester 13, conveniently used as its hydrochloride salt, is condensed with acrylonitrile 14 and the amino group of the product formed is protected, for example, as its tert-butoxycarbonyl (Boc) derivative, to provide 15, which is reduced to the primary amine 16. The ester 16 can be hydrolyzed to the acid 17 and cyclized by using amino acid coupling reagents such as EDC to provide intermediate 2a.

SCHEME 6

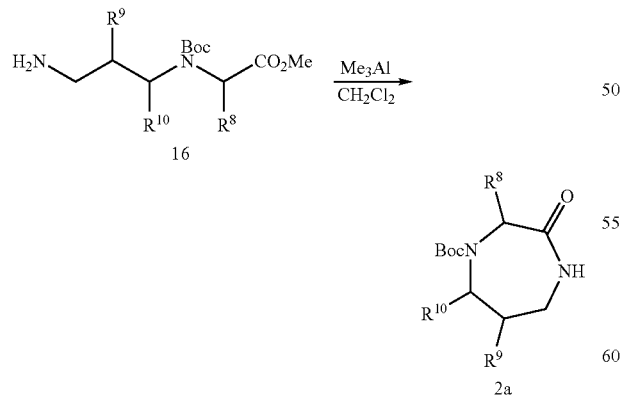

Alternatively, cyclization of 16 from Scheme 5 to N-protected hexahydrodiazepinone 2a can be conducted by using trimethylaluminum, conveniently in dichloromethane, as shown in Scheme 6.

SCHEME 7

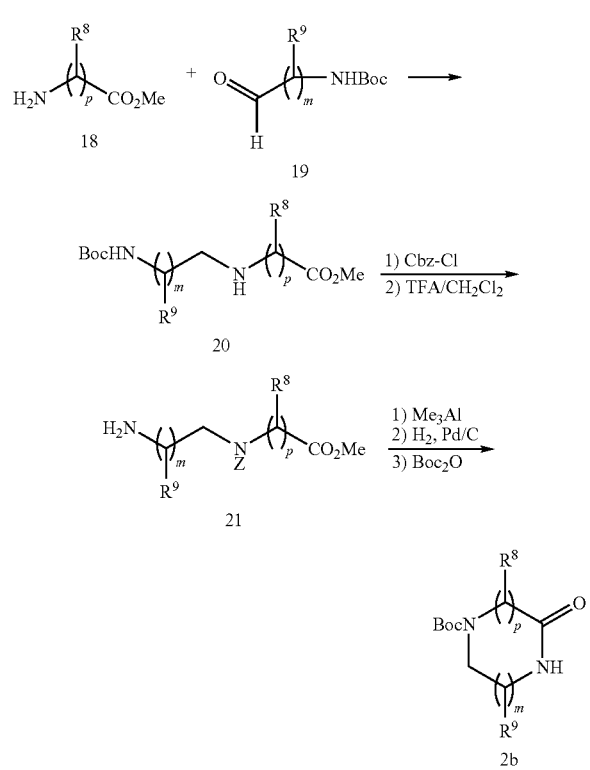

Staring material 2b, wherein $R^{10}$ is hydrogen, may be prepared as illustrated in Scheme 7. Amino ester 18 and N-Boc aminoaldehyde 19 are condensed under reductive amination conditions to provide amine 20. Protection of the newly formed secondary amine, for example as its Z derivative by treatment with carbobenzyloxy chloride, followed by deprotection of the other amine under acidic conditions gives amine 21. Cyclization mediated by trimethylaluminum followed by protecting group manipulation gives the desired intermediate 2b.

SCHEME 8

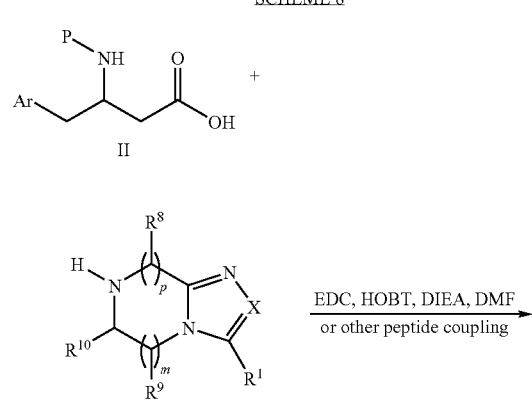

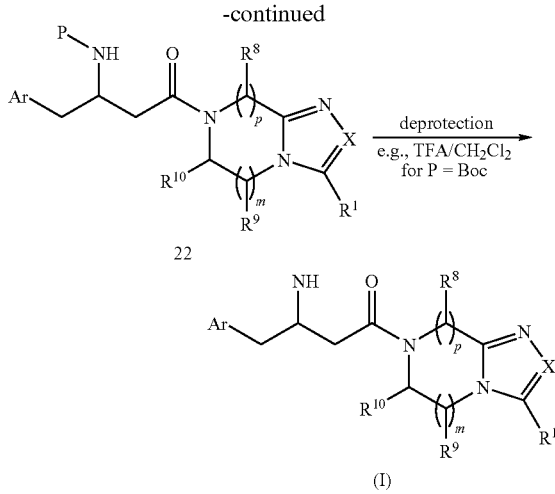

Intermediates II and III are coupled under standard peptide coupling conditions, for example, using 1-ethyl-3-3-dimethylaminopropyl)carbodiimide and 1-hydroxybenzotriazole (EDC/HOBT) or O-(7-azabenzotriazol-1-yl)-N,N,N',N'-tetramethyluronium hexafluorophosphate and 1-hydroxy-7-azabenzotriazole (HATU/HOAT) in a solvent such as N,N-dimethylformamide (DMF) or dichloromethane for 3 to 48 hours at ambient temperature to provide Intermediate 22 as shown in Scheme 8. In some cases, Intermediate III may be a salt, such as a hydrochloride or trifluoroacetic acid salt, and in these cases it is convenient to add a base, generally N,N-diisopropylethylamine, to the coupling reaction. The protecting group is then removed with, for example, trifluoroacetic acid or methanolic hydrogen chloride in the case of Boc to give the desired amine I. The product is purified, if necessary, by recrystallization, trituration, preparative thin layer chromatography, flash chromatography on silica gel, such as with a Biotage® apparatus, or HPLC. Compounds that are purified by HPLC may be isolated as the corresponding salt. Purification of intermediates is achieved in the same manner.

In some cases the product I or synthetic intermediates illustrated in the above schemes may be further modified, for example, by manipulation of substituents on Ar, X, $R^1$, $R^8$, $R^9$, or $R^{10}$. These manipulations may include, but are not limited to, reduction, oxidation, alkylation, acylation, and hydrolysis reactions that are commonly known to those skilled in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

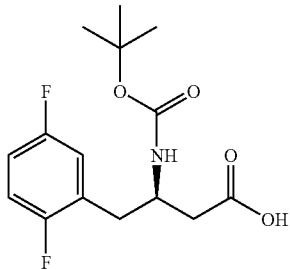

(3R)-3-[(tert-Butoxycarbonyl)amino]-4-(2,5-difluorophenyl)butanoic acid

Step A: (R,S)-N-(tert-Butoxycarbonyl)-2,5-difluorophenylalanine

To a solution of 0.5 g (2.49 mmol) of 2,5-difluoro-DL-phenylalanine in 5 mL of tert-butanol were added sequentially 1.5 mL of 2 N aqueous sodium hydroxide solution and 543 mg of di-tert-butyl dicarbonate. The reaction was stirred at ambient temperature for 16 h and diluted with ethyl acetate. The organic phase was washed sequentially with 1 N hydrochloric acid and brine, dried over magnesium sulfate and concentrated in vacuo. The crude material was purified by flash chromatography (silica gel, 97:2:1 dichloromethane: methanol:acetic acid) to afford the title compound. MS 302 (M+1).

Step B: (R,S)-3-[(tert-Butoxcarbonyl)amino]-1-diazo-4-(2,5-difluoro-phenyl)butan-2-one To a solution of 2.23 g (7.4 mmol) of (R,S)-N-(tert-butoxycarbonyl)-2,5-difluorophenylalanine in 100 mL of diethyl ether at 0° C. were added sequentially 1.37 mL (8.1 mmol) of triethylamine and 0.931 mL (7.5 mmol) of isobutyl chloroformate and the reaction was stirred at this temperature for 15 min. A cooled ethereal solution of diazomethane was then added until the yellow color persisted and stirring was continued for a further 16 h. The excess diazomethane was quenched by dropwise addition of acetic acid, and the reaction was diluted with ethyl acetate and washed sequentially with 5% hydrochloric acid, saturated aqueous sodium bicarbonate solution and brine, dried over magnesium sulfate and concentrated in vacuo. Purification by flash chromatography (silica gel, 4:1 hexane:ethyl acetate) afforded the diazoketone. $^1$H NMR (500 MHz, CDCl$_3$) δ 7.03-6.95 (m, 1H), 6.95-6.88 (m, 2H), 5.43 (bs, 1H), 5.18 (bs, 1H), 4.45 (bs, 1H), 3.19-3.12 (m, 1H), 2.97-2.80 (m, 1H), 1.38 (s, 9H).

Step C: (3R)-3-[(tert-Butoxycarbonyl)amino]-4-(2,5-difluorophenyl)butanoic acid

To a solution of 2.14 g (6.58 mmol) of (R,S)-3-[(tert-butoxycarbonyl)-amino]-1-diazo-4-(2,5-difluorophenyl)butan-2-one dissolved in 100 mL of methanol at -30° C. were added sequentially 3.3 mL (19 mmol) of N,N-diisopropylethylamine and 302 mg (1.32 mmol) of silver benzoate. The reaction was stirred for 90 min before diluting with ethyl acetate and washing sequentially with 2 N hydrochloric acid, saturated aqueous sodium bicarbonate, and brine. The organic phase was dried over magnesium sulfate, concentrated in vacuo and the enantiomers were separated by preparative chiral HPLC (Chiralpak AD column, 5% ethanol in hexanes) to give 550 mg of the desired (R)-enantiomer, which eluted first. This material was dissolved in 50 mL of a mixture of tetrahydrofuran:methanol: 1 N aqueous lithium hydroxide (3:1:1) and stirred at 50° C. for 4 h. The reaction was cooled, acidified with 5% dilute hydrochloric acid and extracted with ethyl acetate. The combined organic phases were washed with brine, dried over magnesium sulfate and concentrated in vacuo to give the title compound as a white foamy solid. $^1$H NMR (500 Mz, CDCl$_3$) δ 7.21 (m, 1H), 6.98 (m, 2H), 6.10 (bs, 1H), 5.05 (m, 1H), 4.21 (m, 1H), 2.98 (m, 2H), 2.60 (m, 2H), 1.38 (s, 9H).

INTERMEDIATE 2

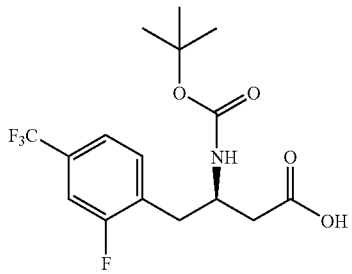

(3R)-3-[(tert-Butoxycarbonyl)amino]-4-[2-fluoro-4-(trifluoromethyl)phenyl]-butanoic acid Step A: (2R,5S)-2,5-Dihydro-3,6-dimethoxy-2-2'-fluoro-4'-(trifluoromethyl)benzyl)-5-isopropylpyrazine To a solution of 3.32 g (18 mmol) of commercially available (2S)-2,5-dihydro-3,6-dimethoxy-2-isopropylpyrazine in 100 mL of tetrahydrofuran at –70° C. was added 12 mL (19 mmol) of a 1.6M solution of butyllithium in hexanes. After stirring at this temperature for 20 min, 5 g (19.5 mmol) of 2-fluoro-trifluoromethylbenzyl bromide in 20 mL of tetrahydrofuran was added and stirring was continued for 3 h before warming the reaction to ambient temperature. The reaction was quenched with water, concentrated in vacuo, and extracted with ethyl acetate. The combined organic phase was washed with brine, dried, and concentrated in vacuo. Purification by flash chromatography (silica gel, 0-5% ethyl acetate in hexanes) afforded the title compound.
$^1$H NMR (500 MHz, CDCl$_3$) δ 7.33-7.25 (m, 3H), 4.35-4.31 (m, 1H), 3.75 (s, 3H), 3.65 (s, 3H), 3.60 (t, 1H, J=3.4 Hz), 3.33 (dd, 1H, J=4.6, 13.5 Hz), 3.03 (dd, 1H, J=7, 13.5 Hz), 2.25-2.15 (m, 1H), 1.0 (d, 3H, J=7 Hz), 0.66 (d, 3H, J=7 Hz).

Step B: (R)-N-(tert-Butoxycarbonyl)-2-fluoro-4-trifluoromethyl-phenylalanine methyl ester To a solution of 5.5 g (15 mmol) of (2R,5S)-2,5-dihydro-3,6-dimethoxy-2-2'-fluoro-4'-(trifluoromethyl)benzyl)-5-isopropylpyrazine in 50 mL of a mixture of acetonitrile:dichloromethane (10:1) was added 80 mL of 1 N aqueous trifluoroacetic acid. The reaction was stirred for 6 h and the organic solvents were removed in vacuo. Sodium carbonate was added until the solution was basic (>pH 8), and then the reaction was diluted with 100 mL of tetrahydrofuran and 10 g (46 mmol) of di-tert-butyl dicarbonate was added. The resulting slurry was stirred for 16 h, concentrated in vacuo, and extracted with ethyl acetate. The combined organic phase was washed with brine, dried, and concentrated in vacuo. Purification by flash chromatography (silica gel, 20% ethyl acetate in hexanes) afforded the title compound. $^1$H NMR (500 MHz, CDCl$_3$) δ 7.38-7.28 (m, 3H), 5.10 (bd, 1H), 4.65-3.98 (m, 1H), 3.76 (s, 3H), 3.32-3.25 (m, 1H), 3.13-3.05 (m, 1H), 1.40 (s, 9H).

Step C: (R)-N-(tert-Butoxycarbonyl)-2-fluoro-4-trifluoromethyl)phenyl-alanine

A solution of 5.1 g (14 mmol) of (R,S)-N-(tert-butoxycarbonyl)-2-fluoro-4-trifluoromethyl)phenylalanine methyl ester in 350 mL of a mixture of tetrahydrofuran:methanol: 1 N lithium hydroxide (3:1:1) was stirred at 50° C. for 4 h. The reaction was cooled, acidified with 5% hydrochloric acid and extracted with ethyl acetate. The combined organic phases were washed with brine, dried over magnesium sulfate and concentrated in vacuo to give the title compound. $^1$H NMR (500 MHz, CD$_3$OD) δ 7.45-7.38 (m, 3H), 4.44-4.40 (m, 1H), 3.38-3.33 (m, 1H), 2.98 (dd, 1H, J=9.6, 13.5 Hz), 1.44 (s, 9H).

Step D: (3R)-3-[(tert-Butoxycarbonyl)amino]-4-[2-fluoro-4-trifluoromethyl)-phenyl]butanoic acid To a solution of 3.4 g (9.7 mmol) of the product from Step C in 60 mL of tetrahydrofuran at 0° C. were added sequentially 2.3 mL (13 mmol) of N,N-diisopropylethylamine and 1.7 mL (13 mmol) of isobutyl chloroformate and the reaction was stirred at this temperature for 30 min. A cooled ethereal solution of diazomethane was then added until the yellow color persisted and stirring was continued for a further 16 h. The excess diazomethane was quenched by dropwise addition of acetic acid, and the reaction was diluted with ethyl acetate and washed sequentially with 5% hydrochloric acid, saturated aqueous sodium bicarbonate solution and brine, dried over magnesium sulfate and concentrated in vacuo. Purification by flash chromatography (silica gel, 9:1 hexane/ethyl acetate) afforded 0.5 g of diazoketone. To a solution of 0.5 g (1.33 mmol) of the diazoketone dissolved in 100 mL of methanol at 0 °C. were added sequentially 0.7 mL (4 mmol) of N,N-diisopropylethylamine and 32 mg (0.13 mmol) of silver benzoate. The reaction was stirred for 2 h before diluting with ethyl acetate and washing sequentially with 2 N hydrochloric acid, saturated aqueous sodium bicarbonate, and brine. The organic phase was dried over magnesium sulfate, concentrated in vacuo and dissolved in 50 mL of a mixture of tetrahydrofuran:methanol: 1 N aqueous lithium hydroxide (3:1:1) and stirred at 50° C. for 3 h. The reaction was cooled, acidified with 5% hydrochloric acid and extracted with ethyl acetate. The combined organic phases were washed with brine, dried over magnesium sulfate and concentrated in vacuo to give the title compound as a white foamy solid. $^1$H NMR (500 MHz, CD$_3$OD) δ 7.47-7.33 (m, 3H), 4.88 (bs, 1H), 4.26-3.98 (m, 1H), 3.06-3.01 (m, 1H), 2.83-2.77 (m, 1H), 2.58-2.50 (m, 2H), 1.29 (s, 9H).

INTERMEDIATE 3

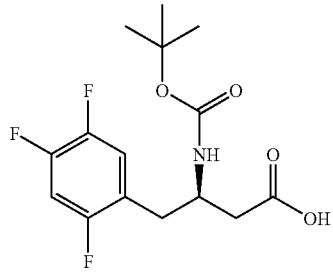

(3R)-3-[(tert-Butoxycarbonyl)amino]-4-(2,4,5-trifluorophenyl)butanoic acid

Step A: (2S,5R)-2,5-Dihydro-3,6-dimethoxy-2-isopropyl-5-(2',4',5'-trifluorobenzyl)-pyrazine The title compound (3.81 g) was prepared from 3.42 g (18.5 mmol) of (2S)-2,5-dihydro-3,6-dimethoxy-2-isopropylpyrazine and 5 g (22.3 mmol) of 2,4,5-trifluorobenzyl bromide using the procedure described for Intermediate 2, Step A.

¹H NMR (500 MHz, CDCl₃):δ 7.01 (m, 1H), 6.85 (m, 1H), 4.22 (m, 1H), 3.78 (m, 3H), 3.64 (m, 3H), 3.61 (m, 1H), 3.20 (m, 1H), 2.98 (m, 1H), 2.20 (m, 1H), 0.99 (d, 3H, J=8 Hz), 0.62 (d, 3H, J=8 Hz).

Step B: (R)-N-(tert-Butoxycarbonyl)-2,4,5-trifluorophenylalanine methyl ester

To a solution of 3.81 g (11.6 mmol) of (2S, 5R)-2,5-dihydro-3,6-dimethoxy-2-isopropyl-5-2',4',5'trifluorobenzyl)pyrazine in 20 mL of acetonitrile was added 20 mL of 2 N hydrochloric acid. The reaction was stirred for 72 h and concentrated in vacuo. The residue was dissolved in 30 mL of dichloromethane and 10 mL (72 mmol) of triethylamine and 9.68 g (44.8 mmol) of di-tert-butyl dicarbonate were added. The reaction was stirred for 16 h, diluted with ethyl acetate and washed sequentially with 1 N hydrochloric acid and brine. The organic phase was dried over sodium sulfate, concentrated in vacuo and purified by flash chromatography (silica gel, 9:1 hexanes:ethyl acetate) to afford the title compound. ¹H NMR (500 MHz, CDCl₃) δ 6.99 (m, 1H), 6.94 (m, 1H), 5.08 (m, 1H), 4.58 (m, 1H), 3.78 (m, 3H), 3.19 (m, 1H), 3.01 (m, 1H), 1.41 (s, 9H).

Step C: (R)-N-(tert-Butoxycarbonyl)-2,4,5-trifluorophenylalanine

The title compound (2.01 g) was prepared from 2.41 g (7.5 mol) of (R)-N-tert-butoxycarbonyl)-2,4,5-trifluorophenylalanine methyl ester using the procedure described for Intermediate 2, Step C. LC-MS 220.9 (M+1−BOC).

Step D: (3R)-3-[(tert-Butoxycarbonyl)amino]-4-(2,4,5-trifluorophenyl)-butanoic acid To a solution of 0.37 g (1.16 mmol) of (R)-N-(1,1-dimethylethoxy-carbonyl)-2,4,5-trifluorophenylalanine in 10 mL of diethyl ether at −20° C. were added sequentially 0.193 mL (1.3 mmol) of triethylamine and 0.18 mL (1.3 mmol) of isobutyl chloroformate, and the reaction was stirred at this temperature for 15 min. A cooled ethereal solution of diazomethane was then added until the yellow color persisted and stirring was continued for a further 1 h. The excess diazomethane was quenched by dropwise addition of acetic acid, and the reaction was diluted with ethyl acetate and washed sequentially with saturated aqueous sodium bicarbonate solution and brine, dried over magnesium sulfate and concentrated in vacuo. Purification by flash chromatography (silica gel, 3:1 hexane:ethyl acetate) afforded 0.36 g of diazoketone. To a solution of 0.35 g (1.15 mmol) of the diazoketone dissolved in 12 mL of 1,4-dioxane:water (5:1) was added 26 mg (0.113 mmol) of silver benzoate. The resultant solution was sonicated for 2 h before diluting with ethyl acetate and washing sequentially with 1 N hydrochloric acid and brine, drying over magnesium sulfate and concentrating in vacuo. Purification by flash chromatography (silica gel, 97:2:1 dichloromethane:methanol:acetic acid) afforded the title compound.

¹H NMR (500 MHz, CDCl₃) δ 7.06 (m, 1H), 6.95 (m, 1H), 5.06 (bs, 1H), 4.18 (m, 1H), 2.98 (m, 2H), 2.61 (m, 2H), 1.39 (s, 9H).

INTERMEDIATE 4

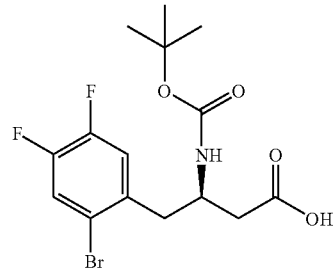

(3R)-4-(2-Bromo-4,5-difluorophenyl)-3-[(tert-butoxycarbonyl)amino]-butanoic acid To a solution of 2.4 g (10 mmol) of 2-bromo-4,5-difluorobenzoic acid [prepared according to the procedure of Braish et al., Syn. Comm., 3067-3074 (1992)] in 75 mL of tetrahydrofuran was added 2.43 g (15 mmol) of 1,1'-carbonyldiimidazole. The solution was heated under reflux for 3.5 h, cooled to ambient temperature and 0.38 g (10 mmol) of sodium borohydride in 15 mL of water was added. The reaction was stirred for 10 min and partitioned between ethyl acetate and 10% aqueous sodium bicarbonate solution. The organic layer was washed twice with warm water, brine, dried over magnesium sulfate, and concentrated in vacuo. Purification by flash chromatography (silica gel, 4:1 hexane:ethyl acetate) afforded 1.9 g of 2-bromo-4,5-difluorobenzyl alcohol. To a solution of 1.9 g (8.4 mmol) of 2-bromo-4,5-difluorobenzyl alcohol in 30 mL of dichloromethane at 0° C. was added 3.4 g (10 mmol) of carbon tetrabromide and 2.7 g (10 mmol) of triphenylphosphine. The reaction was stirred for 2 h at this temperature, the solvent was removed in vacuo and the residue stirred with 100 mL of diethyl ether. The solution was filtered, concentrated in vacuo, and purified by flash chromatography (silica gel, 20:1 hexane:ethyl acetate) to afford 2.9 g of 2-bromo-4,5-difluorobenzyl bromide contaminated with carbon tetrabromide which was used without further purification. Using the procedures outlined for the preparation of Intermediates 2-4, the benzyl bromide derivative was converted to the title compound. LC-MS 394 and 396 (M+1).

Essentially following the procedures outlined for the preparation of Intermediates 1-4, the Intermediates in Table 1 were prepared.

TABLE 1

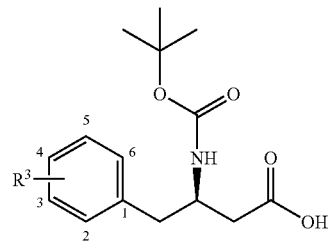

| Intermediate | R³ | Selected ¹H NMR data (CD₃OD) |
|---|---|---|
| 5 | 2-F, 4-Cl, 5-F | 7.11(dd, 1H, J=8.9, 6.4Hz), 7.03(dd, 1H, J=9.0, 6.6) |
| 6 | 2-F, 5-Cl | 7.27(dd, 1H, J=6.4, 2.5Hz), 7.21(m. 1H), 7.03(t, 1H, J=9.2Hz) |

TABLE 1-continued

| Inter-mediate | R³ | Selected ¹H NMR data (CD₃OD) |
|---|---|---|
| 7 | 2-Me, 5-Cl | 7.16(d, 1H, J=1.8Hz), 7.11-7.07(m, 2H), 2.34(s, 3H) |
| 8 | 2-Cl, 5-Cl | 7.34(d, 1H, J=9.0), 7.33(d, 1H, J=2.1 Hz), 7.21(dd, 1H, J=8.5, 2.5Hz) |
| 9 | 2-F, 3-Cl, 6-F | 7.35(td, 1H, J=8.5, 5.8Hz), 6.95(t, 1H, J=8.5 Hz) |
| 10 | 3-Cl, 4-F | 7.33(d, 1H, J=6.9Hz), 7.19-7.11(m, 2H) |
| 11 | 2-F, 3-F, 6-F | 7.18-7.12(m, 1H), 6.91(m, 1H) |
| 12 | 2-F, 4-F, 6-F | 6.81(t, 2H, J=8.4Hz) |
| 13 | 2-OCH₂Ph, 5-F | 7.49(d, 2H, J=7.6Hz), 7.38(t, 2H, J=7.3 Hz), 7.30(t, 1H, J=7.3Hz), 6.96-6.89(m, 3H), 5.11(d, 1H, J=11.7Hz), 5.08(d, 1H, J=11.9 Hz) |

EXAMPLE 1

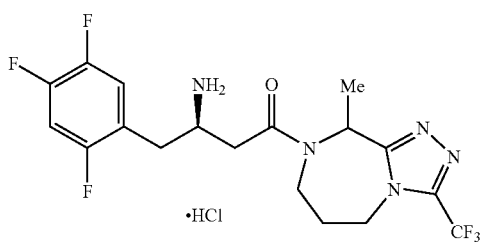

8-[(3R)-3-Amino-4-(2,4,5-trifluorophenyl)butanoyl]-9-methyl-3-(trifluoromethyl)-6,7,8,9-tetrahydro-5H-[1,2,4]triazolo[4,3-a][1,4]diazepine, hydrochloride Step A: Methyl N-(tert-butoxycarbonyl)-N-(2-cyanoethyl)-D-alaninate To a stirred suspension of D-alanine methyl ester hydrochloride (2.0 g) and 5 N aqueous sodium hydroxide solution (2.9 mL) in water (15 mL) at 0° C., acrylonitrile (1.1 mL) was added. The resultant mixture was stirred at 70° C. for 3.5 h and cooled to room temperature. Di-tert butyl dicarbonate (30 mL) was added and the reaction mixture stirred for two days. The reaction mixture was diluted with saturated aqueous sodium bicarbonate solution and extracted with ethyl acetate. The organic layer was separated, washed with brine, dried over anhydrous sodium sulfate and concentrated. The residue was purified by flash column chromatography (silica gel, eluted with ethyl acetate/hexane 2:3) to yield methyl N-(tert-butoxycarbonyl)-N-2-cyanoethyl)-D-alaninate. MS 256.9 (M+1)

Step B: Methyl N-(3-aminopropyl)-N-(tert-butoxycarbonyl)-D-alaninate

To a solution of methyl N-tert-butoxycarbonyl)-N-2-cyanoethyl)-D-alaninate (1.5 g) in ethanol (80 mL) and chloroform (1.4 mL) was added platinum oxide (350 mg), and the reaction mixture was stirred over an atmosphere of hydrogen for 16 h. The mixture was filtered through Celite, and the Celite washed with methanol and dichloromethane. The filtrate was concentrated to give methyl N-(3-aminopropyl)-N-(tert-butoxycarbonyl)-D-alaninate as an oily residue. MS 261.0 (M+1)

Step C: tert-Butyl(2R)-Hexahydro-2-methyl-3-oxo-1H-1,4-diazepine-1-carboxylate

To a 2M solution of trimethylaluminum in dichloromethane (30 mL) was added slowly a solution of methyl N-(3-aminopropyl)-N-(tert-butoxycarbonyl)-D-alaninate (11.5 g) in dichloromethane. The reaction mixture was stirred at room temperature for four days and then poured into a flask containing 30 g of Celite. The mixture was stirred and quenched by the slow addition of about 10 mL of saturated aqueous ammonium chloride solution. Sodium sulfate (20 g) and methanol (50 mL) were added. The mixture was stirred for 1 h, then filtered. The solids were washed with 5% methanol/dichloromethane. The filtrate was concentrated. The residue was purified by flash chromatography (silica gel, eluting sequentially with 4, 6, 7 and 12% of 10:1 methanoνaqueous concentrated ammonium hydroxide in dichloromethane) to provide the title compound containing less than 3% of the (3S)-isomer. MS 228.9 (M+1).

Step D: (3R)-Hexahydro-3-methyl-2H-1,4-diazepin-2-one hydrochloride

A sample of tert-butyl (2R)-hexahydro-2-methyl-3-oxo-1H-1,4-diazepine-1-carboxylate obtained in the previous step was dissolved in 4M hydrogen chloride in dioxane and evaporated after 2.5 h to yield the hydrochloride salt of the desired compound. MS 129.0 (M+1)

Step E: tert-Butyl 3-methoxy-2-methyl-2,5,6,7-tetrahydro-1H-1,4-diazepine-1-carboxylate To a stirred solution of lactam from Step D (275 mg, 1.20 mmol) in dichloromethane (6 mL) was added trimethyloxonium tetrafluoroborate (207 mg, 1.40 mmol) and the reaction mixture was stirred at room temperature overnight. The reaction mixture was quenched with saturated aqueous sodium bicarbonate solution, extracted twice with ethyl acetate. The organic layer was washed with brine, dried over sodium sulfate and concentrated to yield the title compound, which was used in the next step without purification. MS 242.9 (M+1)

Step F: tert-Butyl 9-methyl-3-(trifluoromethyl)-6,7-dihydro-5H-[1,2,4]triazolo[4,3-a][1,4]diazepine-8(9H)-carboxylate To a solution of hydrazine (0.090 mL, 3.0 mmol) in dichloromethane (3mL) was added the compound from Step E (297 mg, 1.23 mmol), and the resultant mixture was stirred at room temperature for 3 h. The reaction mixture was concentrated under reduced pressure and stripped with toluene twice to remove excess hydrazine. The residue was dried under vacuum overnight and then dissolved in dichloromethane (10 mL and treated with triethylamine (0.42 mL, 3.0 mmol) and trifluoroacetic anhydride. The resultant mixture was heated at 35° C. for 2 h. Solvent was removed, and the residue was evaporated twice with toluene to dryness. The resultant oily residue was dissolved in n-BuOH and heated at 120° C. overnight. After solvent was removed, the residue was purified by flash chromatography (silica gel, eluting with 3% of 10% methanolic ammonium hydroxide in dichloromethane) to yield the desired compound. MS 321.0 (M+1)

Step G: 9-Methyl-3-(trifluoromethyl)-6,7,8,9-tetrahydro-5H-[1,2,4]triazolo[4,3-a][1,4]diazepine hydrochloride Compound from Step F (220 mg, 0.68 mmol) was treated with 4 N hydrogen chloride in dioxane at ambient temperature for 2 h. Concentration gave the title compound. MS 220.9 (M+1)

Step H: 8-[(3R)-3-Amino-4-(2,4,5-trifluorophenyl)butanoyl]-9(R or S)-methyl-3-(trifluoromethyl)-6,7,8,9-tetrahydro-5H-[1,2,4]triazolo[4,3-a][1,4]diazepine, hydrochloride and 8-[(3R)-3-amino-4-(2,4,5-trifluorophenyl)butanoyl]-9(S or R)-methyl-3-(trifluoromethyl)-6,7,8,9-tetrahydro-5H-[1,2,4]triazolo[4,3-a][1,4]diazepine, hydrochloride To a stirred solution of (3R)-3-[(tert-butoxycarbonyl)amino]-4-(2,4,5-trifluorophenyl)butanoic acid (119 mg, 0.358 mmol), EDC (82 mg, 0.430 mmol) and HOBT (58 mg, 0.430 mmol) in DMF (3 mL) at room temperature under nitrogen was added a mixture of 9-methyl-3-(trifluoromethyl)-6,7,8,9-tetrahydro-5H-[1,2,4]triazolo[4,3-a][1,4]diazepine hydrochloride from Step G (90 mg, 0.351 mmol) and triethylamine in DMF (3 mL). The resultant mixture was stirred at ambient temperature for 4 days. Then the reaction mixture was diluted with saturated aqueous sodium bicarbonate solution and extracted with ethyl acetate. The organic layer was washed with brine, dried over sodium sulfate, and concentrated. The residue was purified by preparative thin layer chromatography (5% of 10% methanolic ammonium hydroxide in dichloromethane) to yield the N-BOC precursors of the title compound as a mixture of diastereomers. Chiral HPLC separation (ChiralCel OD column, 6% ethanol/hexane) provided the individual diastereomers, each of which was treated with 4 N hydrogen chloride in dioxane at ambient temperature for 2 h. Concentration gave the individual diastereomers of the title compound. Faster eluting diastereomer: MS 436.0 (M+1); slower eluting diastereomer: MS 436.0 (M+1).

EXAMPLE 2

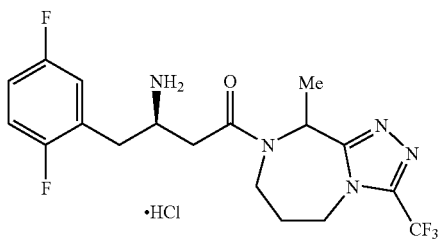

8-[(3R)-3-Amino-4-(2,5-difluorophenyl)butanoyl]-9(R or S)-methyl-3-(trifluoromethyl)-6,7,8,9-tetrahydro-5H-[1,2,4]triazolo[4,3-a][1,4]diazepine, hydrochloride and 8-[(3R)-3-amino-4-(2,5-difluorophenyl)butanoyl]-9(S or R)-methyl-3-(trifluoromethyl)-6,7,8,9-tetrahydro-5H-[1,2,4]triazolo[4,3-a][1,4]diazepine, hydrochloride The title compound was made essentially following the sequence of steps described in Example 1, coupling with (3R)-3-[(tert-butoxycarbonyl)amino]4-(2,5-trifluorophenyl)butanoic acid. Faster eluting diastereomer: MS 418.0 (M+1); slower eluting diastereomer: MS 418.0 (M+1).

EXAMPLE 3

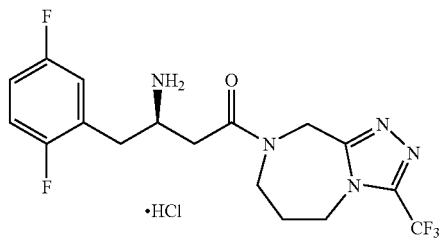

8-[(3R)-3-Amino-4-(2,5-difluorophenyl)butanol]-3-trifluoromethyl)-6,7,8,9-tetrahydro-5H-[1,2,4]triazolo[4,3-a][1,4]diazepine, hydrochloride Step A: Methyl N-(3-Aminopropyl)-N-(tert-butoxycarbonyl)glycinate The title compound was prepared from glycine methyl ester hydrochloride following the methods described in Example 1, Steps A-B. MS 247.0 (M+1).

Step B: tert-Butyl Hexahydro-3-oxo-1H-1,4-diazepine-1-carboxylate

To a solution of methyl N-(3-aminopropyl)-N-(tert-butoxycarbonyl)glycinate (10.2 g) in tetrahydrofuran (THP)/methanol (2/1, 300 mL) was added 1M aqueous lithium hydroxide solution (60 mL). The resultant mixture was stirred at room temperature overnight. An additional 20 ML of 1M aqueous lithium hydroxide solution was added and the mixture was stirred for 6 h. Solvent was removed under reduced pressure, and the residue was dissolved in 50 mL of methanol and 200 mL of toluene and concentrated in vacuo. To the residue in dichloromethane (300 mL) was added 1-ethyl-3-(3-dimethylaminopropyl)carbodiimide (EDC, 9.6 g) and 1-hydroxybenzotriazole (HOBT, 6.8 g). The mixture was stirred at room temperature for three days, then treated with saturated aqueous ammonium chloride solution and extracted with three portions of ethyl acetate. The combined organics were washed with brine, dried over sodium sulfate and concentrated. The residue was purified by chromatography (silica gel, eluting with 4 to 5% [10:1 methanol/aqueous ammonium hydroxide] in dichloromethane) to yield the title compound. MS 215.0 (M+1).

Step C: Hexahydro-2H-1,4-diazepin-2-one hydrochloride

Compound from Step B was treated with 4 N hydrogen chloride in dioxane at ambient temperature for 2.5 h. Concentration gave the title compound.

Step D: 3-(Trifluoromethyl-6,7,8,9-tetrahydro-5H-[1,2,4]triazolo[4,3-a][1,4]diazepine hydrochloride The title compound was prepared from the lactam from Step C essentially following the procedure outlined in Example 1, Steps E-G. MS 207.1 (M+1)

Step E: (2R)-1-(2,5-Trifluorophenyl)-4-[9-methyl-3-trifluoromethyl)-6,7-dihydro-5H-[1,2,4]triazolo[4,3-a][1,4]diazepin-8(9H)-yl]-4-oxobutan-2-amine hydrochloride To a stirred solution of (3R)-3-[(tert-butoxycarbonyl)amino]4-(2,5-difluorophenyl)butanoic acid (45 mg, 0.143 mmol), EDC (29 mg, 0.152 mmol) and HOBT (21 mg, 0.152 mmol) in dichloromethane (2.5 mL) at ambient temperature under nitrogen was added 3-(trifluoromethyl)-6,7,8,9-tetrahydro-5H-[1,2,4]triazolo[4,3-a][1,4]diazepine hydrochloride (70 mg, 0.34 mmol) from Step D. The resultant mixture was stirred at ambient temperature overnight and concentrated. The residue was purified by preparative thin layer chromatography (6% of 10% methanolic ammonium hydroxide solution in dichloromethane) to give the N-BOC precursor, which was dissolved in 2 N methanolic hydrogen chloride. After stirring at ambient temperature for 6 h, concentration yielded the title compound. MS 404 (M+1).

EXAMPLE 4

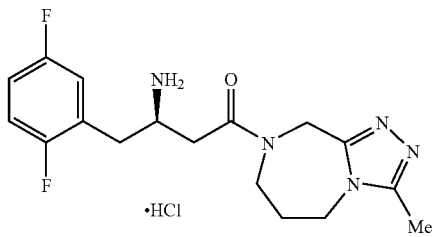

8-[(3R)-3-Amino-4-(2,5-difluorophenyl)butanoyl]-3-methyl-6,7,8,9-tetrahydro-5H-[1,2,4]triazolo[4,3-a][1,4]diazepine, hydrochloride The title compound was made essentially following the methods described in Example 3. MS 350.1 (M+1).

EXAMPLE 5

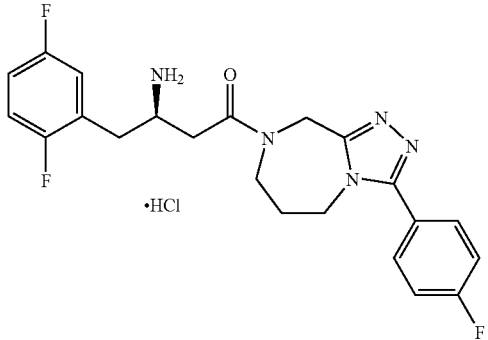

8-[(3R)-3-Amino-4-(2,5 difluorophenyl)butanoyl]-3-4-fluorophenyl)-6,7,8,9-tetrahydro-5H-[1,2,4]triazolo[4,3-a][1,4]diazepine, hydrochloride The title compound was made essentially following the methods described in Example 3. MS 430.2 (M+1).

EXAMPLE 6

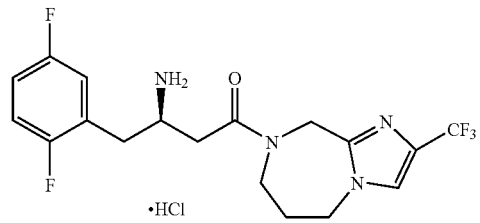

8-[(3R)-3-Amino-4-(2,5-difluorophenyl)butanoyl]-3-(trifluoromethyl)-6,7,8,9-tetrahydro-5H-imidazo[1,2-a][1,4]diazepine, hydrochloride Step A: tert-Butyl 3-methoxy-2,5,6,7-tetrahydro-1H-1,4-diazepine-1-carboxylate To a stirred solution of lactam from Example 3, Step B (2.0 g, 9.34 mmol) in dichloromethane (10 mL) was added trimethyloxonium tetrafluoroborate (1.51 g, 10.2 mmol). The resultant mixture was stirred at ambient temperature overnight. The reaction mixture was quenched with saturated sodium bicarbonate solution and extracted with two portions of ethyl acetate. The organic layer was washed with brine, dried over sodium sulfate, and concentrated to yield the oily product, which was used without purification.

Step B: tert-Butyl 3-imino-1,4-diazepine-1-carboxylate hydrochloride

To a stirred solution of imino methyl ether from Step A (1.75 g, 7.66 mmol) in ethanol was added ammonium chloride (0.4 g, 7.68 mmol). The resultant mixture was refluxed for 4 h. Concentration gave the title compound.

Step C: 2-(Trifluoromethyl)-6,7,8,9-tetrahydro-5H-imidazo[1,2-a][1,4]diazepine

To a stirred mixture of compound from Step B (0.42 g, 1.68 mmol) and triethylamine (0.64 mL, 4.6 mmol) in dioxane was added 1-bromo-3,3,3-trifluoroacetone. The resultant mixture was heated at 50° C. overnight. After solvent was removed, the residue was dissolved in isopropanol and refluxed overnight. After an aqueous work-up, the residue purified by flash chromatography (silica gel, 4% of 10% methanolic ammonium hydroxide solution in dichloromethane). The intermediate was dissolved in acidic (three drops of concentration hydrochloric acid) methoxyethanol (8 mL) and heated at 120° C. overnight. After solvent was removed, the residue was treated with 4 N hydrogen chloride in dioxane for 3 h. Purification by flash chromatography (silica gel, eluting with 6% of 10% methanolic ammonium hydroxide in dichloromethane) gave the title compound.

Step D: 8-[(3R)-3-Amino-4-2,5-difluorophenyl)butanoyl]-3-(trifluoromethyl)-6,7,8,9-tetrahydro-5H-imidazo[1,2-a][1,4]diazepine, hydrochloride The title compound was made from (3R)-3-[(tert-butoxycarbonyl)amino]-4-(2,5-difluorophenyl)butanoic acid and 2-(trifluoromethyl)-6,7,8,9-tetrahydro-5H-imidazo[1,2-a]

[1,4]diazepine from Step C essentially following the procedure described in Example 3, Step E. MS 206.0 (M+1)

EXAMPLE 7

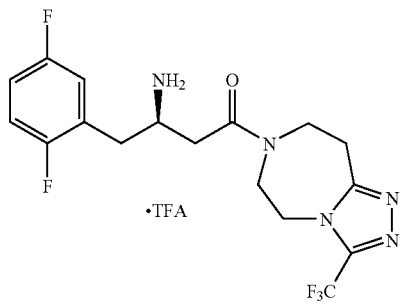

7-[(3R)-3-Amino-4-(2,5-difluorophenyl)butanoyl]-3-(trifluoromethyl)-6,7,8,9-tetrahydro-5H-[1,2,4]triazolo[4,3-d][1,4]diazepine, trifluoroacetic acid salt Step A: 1-Benzyl-1,4-diazepane-5-thione To a solution of 1-benzyl-1,4-diazepan-5-one (2.00 g, 9.80 mmol) in anhydrous dioxane (40 mL), sodium bicarbonate (8.81 g, 105 mmol) and phosphorus pentasulfide (2.92 g, 13.1 mmol) were added. The mixture was heated to 75° C. for 6 h. Dioxane was removed under reduced pressure and the residue was treated with water (80 mL). The resultant mixture was stirred at 50° C. for 1 h and then stirred an additional 2 h at 25° C. Sodium chloride (30.0 g) was added to the mixture and the aqueous phase was extracted with dichloromethane. The organic phase was concentrated to yield the desired compound, which was used without further purification.

Step B: (5Z)-1-Benzyl-1,4-diazepan-5-one hydrazone

To a solution of the compound from Step A (1.00 g, 4.54 mmol) in 2-propanol (8.0 mL) and THF (20 mL), hydrazine (0.68 g, 21.7 mmol) was added. The mixture was stirred at room temperature overnight. The crude product was concentrated, and the residue purified by preparative TLC (silcia gel, 1:9 10% ammonium hydroxide in methanol:dichloromethane) to yield the desired compound.

Step C: 7-Benzyl-3-trifluoromethyl)-6,7,8,9-tetrahydro-5H-[1,2,4]triazolo[4,3-d][1,4]diazepine To a solution of the compound from Step B (0.26 mg, 1.20 mmol) in anhydrous dichloromethane (10 mL), trifluoroacetic anhydride (0.47 mL, 3.31 mmol) and trifluoroacetic acid (1.82 mL, 23.6 mmol) were added. The mixture was heated to 40° C. for 1 h. The solvent was removed under reduced pressure. The residue was heated in toluene with azeotropic removal of water using a Dean-Stark apparatus. After refluxing for 24 h, the toluene was removed under reduced pressure and the crude product was purified by preparative TLC (silica gel, eluting with 8:92 10% ammonium hydroxide in methanol/dichloromethane) to yield the desired compound. MS 297.1 (M+1).

Step D: 3-(Trifluoromethyl)-6,7,8,9-tetrahydro-5H-[1,2,4]triazolo[4,3-d][1,4]diazepine The compound from Step C (0.07 mg, 0.24 mmol) in ethanol (4.0 mL) and glacial acetic acid (2.0 mL) was stirred under an atmosphere of hydrogen in the presence of 10% palladium on carbon (20 mg). The catalyst was removed by filtration through Celite. Concentration of the filtrate provided the desired compound. MS 207.0 (M+1).

Alternatively, the removal of the benzyl group could be conducted as follows: The compound from Step C (0.35 mmol) in dichloromethane (3.0 mL) was treated with 1-chloroethyl chloroformate (0.53 mmol) and heated in a sealed tube at 45° C. overnight. The resultant solution was cooled to room temperature, concentrated, dissolved in methanol (5.0 mL) and heated at 45° C. for 3 h. The solution was evaporated and dried under vacuum to yield the hydrochloride salt of the desired compound.

Step F: 7-[(3R)-3-Amino-4-(2,5-difluorophenyl) butanoyl]-3-(trifluoromethyl)-6,7,8,9-tetrahydro-5H-[1,2,4]triazolo[4,3-d][1,4]diazepine, trifluoroacetic acid salt To a solution of (3R)-3-[(tert-butoxycarbonyl)amino](2,5-difluorophenyl)butanoic acid (0.08 g, 0.24 mmol) and EDC (0.06 g, 0.29 mmol) in anhydrous dichloromethane (3.0 mL) were added compound from Step E (0.06 g, 0.245 mmol) and triethylamine (0.08 mL, 0.54 mmol). The resultant solution was stirred at room temperature overnight and concentrated. Purification by preparative TLC (silica gel, 7:93 10% ammonium hydroxide in methanol:dichloromethane) gave the N-Boc intermediate, which was treated with 1:1 trifluoroacetic acid:dichloromethane to provide the title compound. MS 404.2 (M+1).

EXAMPLE 8

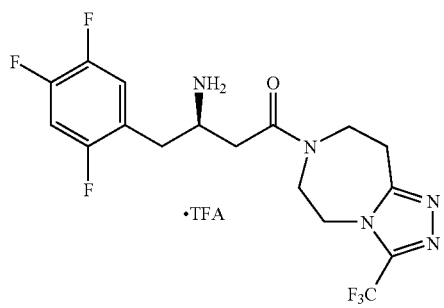

7-[(3R)-3-Amino-4-(2,4,5-trifluorophenyl)butanoyl]-3-(trifluoromethyl)-6,7,8,9-tetrahydro-5H-[1,2,4]triazolo[4,3-d][1,4]diazepine, trifluoroacetic acid salt The title compound was made essentially following the sequence of steps described in Example 7, coupling with (3R)-3-[(tert-butoxycarbonyl)amino]-4-2,4,5-trifluorophenyl)butanoic acid. MS 422.0 (M+1).

EXAMPLE 9

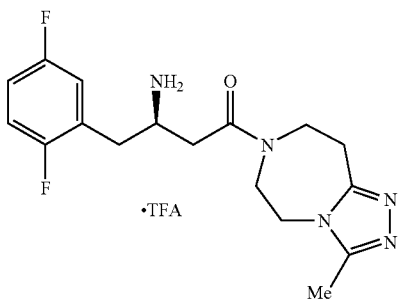

7-[(3R)-3-Amino-4-(2,5-difluorophenyl)butanoyl]-3-methyl-6,7,8,9-tetrahydro-5H-[1,2,4]triazolo[4,3-d][1,4]diazepine, trifluoroacetic acid salt The title compound was made essentially by following the sequence of steps described in Example 7. MS 350.2 (M+1).

EXAMPLE 10

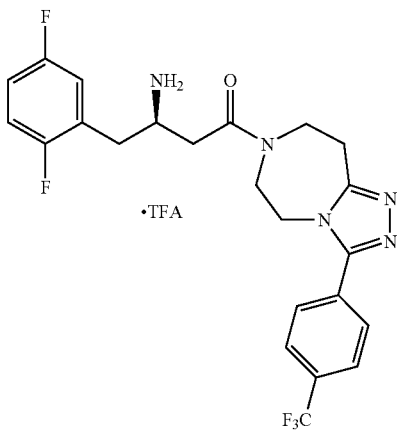

7-[(3R)-3-Amino-4-(2,5-difluorophenyl)butanoyl]-3-[4-(trifluoromethyl)phenyl]-6,7,8,9-tetrahydro-5H-[1,2,4]triazolo[4,3-d][1,4]diazepine, trifluoroacetic acid salt The title compound was made essentially by following the sequence of steps described in Example 7. MS 480.2 (M+1).

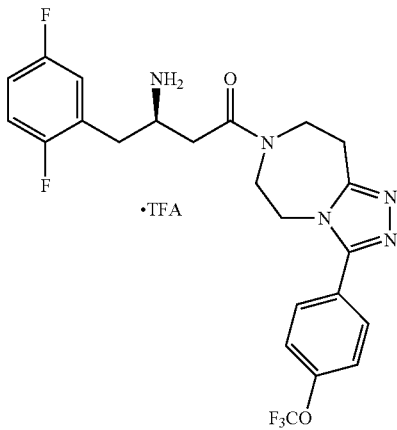

7-[(3R)-3-Amino-4-(2,5-difluorophenyl)butanoyl]-3-[4-(trifluoromethoxy)phenyl]-6,7,8,9-tetrahydro-5H-[1,2,4]triazolo[4,3-d][1,4]diazepine, trifluoroacetic acid salt The title compound was made essentially by following the sequence of steps described in Example 7. MS 496.2 (M+1).

EXAMPLE 12

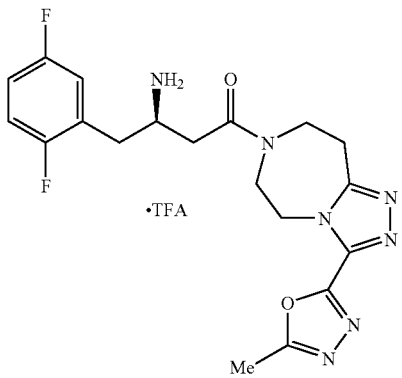

7-[(3R)-3-Amino-4-(2,5-trifluorophenyl)butanoyl]-3-(5-methyl-1,3,4-oxadiazol-2-yl)-6,7,8,9-tetrahydro-5H-[1,2,4]triazolo[4,3-d][1,4]diazepine, trifluoroacetic acid salt The title compound was made essentially by following the sequence of steps described in Example 7. MS 418.3 (M+1).

EXAMPLE OF A PHARMACEUTICAL FORMULATION

As a specific embodiment of an oral pharmaceutical composition, a 100 mg potency tablet is composed of 100 mg of any of the compounds of the present invention, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

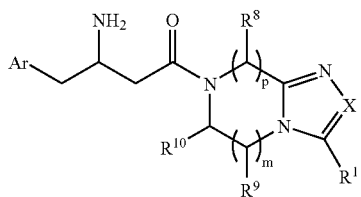

wherein
each n is independently 0, 1, or 2;
m is 1 or 2;
p is 1 or 2; with the proviso that m+p is 3;
X is N or $CR^2$;
Ar is phenyl substituted with one to five $R^3$ substituents;
$R^1$ and $R^2$ are each independently selected from the group consisting of
hydrogen,
halogen,
hydroxy,
cyano,
$C_{1-10}$ alkyl, wherein alkyl is unsubstituted or substituted with one to five substituents independently selected from halogen or hydroxy,
$C_{1-10}$ alkoxy, wherein alkoxy is unsubstituted or substituted with one to five substituents independently selected from halogen or hydroxy,
$C_{1-10}$ alkylthio, wherein alkylthio is unsubstituted or substituted with one to five substituents independently selected from halogen or hydroxy,
$C_{2-10}$ alkenyl, wherein alkenyl is unsubstituted or substituted with one to five substituents independently selected from halogen or hydroxy,
$(CH_2)_n COOH$,
$(CH_2)_n COOC_{1-6}$ alkyl,
$(CH_2)_n CONR^4R^5$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
or $R^4$ and $R^5$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
$(CH_2)_n$—$NR^4R^5$,
$(CH_2)_n$—$OCONR^4R^5$,
$(CH_2)_n$—$SO_2NR^4R^5$,
$(CH_2)_n$—$SO_2R^6$,
$(CH_2)_n$—$NR^7SO_2R^6$,
$(CH_2)_n$—$NR^7CONR^4R^5$,
$(CH_2)_n$—$NR^7COR^7$,
$(CH_2)_n$—$NR^7CO_2R^6$,
$(CH_2)_n$—$COR^6$,
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens,
$(CH_2)_n$-aryl, wherein aryl is unsubstituted or substituted with one to five substituents independently selected from halogen, cyano, hydroxy, $NR^7SO_2R^6$, $SO_2R^6$, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
$(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, and
$(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens,
wherein any methylene ($CH_2$) carbon atom in $R^1$ or $R^2$ is unsubstituted or substituted with one to two groups independently selected from halogen, hydroxy, and $C_{1-4}$ alkyl unsubstituted or substituted with one to five halogens;
each $R^3$ is independently selected from the group consisting of
hydrogen,
halogen,
cyano,
hydroxy,
$C_{1-6}$ alkyl, unsubstituted or substituted with one to five halogens, and
$C_{1-6}$ alkoxy, unsubstituted or substituted with one to five halogens;
$R^6$ is independently selected from the group consisting of tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, and wherein any methylene ($CH_2$) carbon atom in $R^6$ is unsubstituted or substituted with one to two groups independently selected from halogen, hydroxy, $C_{1-4}$ alkyl, and $C_{1-4}$ alkoxy, wherein alkyl and alkoxy are unsubstituted or substituted with one to five halogens;
each $R^7$ is hydrogen or $R^6$;
each $R^8$, $R^9$, and $R^{10}$ is independently selected from the group consisting of
hydrogen,
cyano,
carboxy,
$C_{1-6}$ alkyloxycarbonyl,
$C_{1-10}$ alkyl, unsubstituted or substituted with one to five substituents independently selected from halogen, hydroxy, $C_{1-6}$ alkoxy, carboxy, $C_{1-6}$ alkyloxycarbonyl, and phenyl-$C_{1-3}$ alkoxy, wherein alkoxy is unsubstituted or substituted with one to five halogens,
$(CH_2)_n$-aryl, wherein aryl is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens,
$(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, $(CH_2)_n$-heterocyclyl, wherein heterocyclyl is unsubstituted or substituted with one to three substituents independently selected from oxo, hydroxy, halogen, $C_{1-6}$ alkyl, and $C_{1-6}$ alkoxy, wherein alkyl and alkoxy are unsubstituted or substituted with one to five halogens, $(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens, and $(CH_2)_n CONR^4 R^5$, wherein $R^4$ and $R^5$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

or $R^4$ and $R^5$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

wherein any methylene ($CH_2$) carbon atom in $R^8$, $R^9$ or $R^{10}$ is unsubstituted or substituted with one to two groups independently selected from halogen, hydroxy, and $C_{1-4}$ alkyl unsubstituted or substituted with one to five halogens.

2. The compound of claim 1 of structural formula Ia wherein the carbon atom marked with an * has the R configuration:

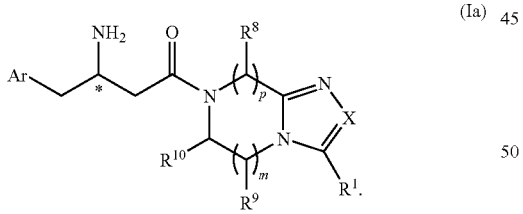

(Ia)

3. The compound of claim 1 of structural formula Ib:

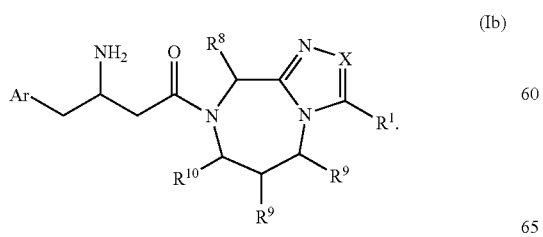

(Ib)

4. The compound of claim 3 of structural formula Ic wherein the carbon atom marked with an * has the R configuration

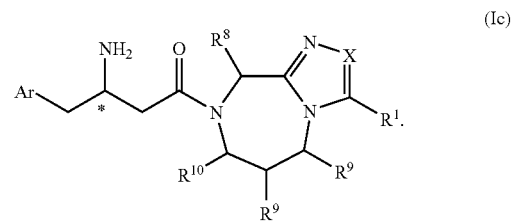

(Ic)

5. The compound of claim 3 of structural formula Id:

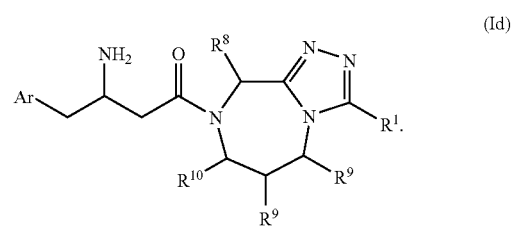

(Id)

6. The compound of claim 3 of structural formula Ie:

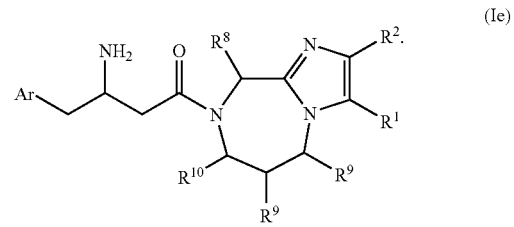

(Ie)

7. The compound of claim 1 of structural formula If:

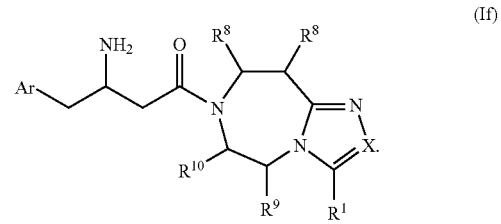

(If)

8. The compound of claim 7 of structural formula Ig wherein the carbon atom marked with an * has the R configuration:

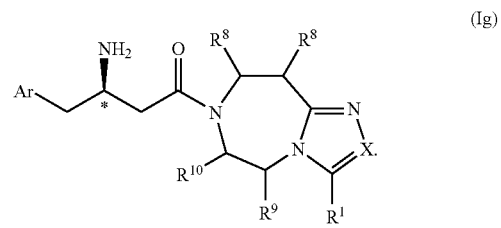

(Ig)

9. The compound of claim 7 of structural formula Ih:

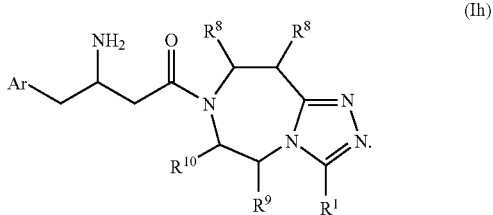

(Ih)

10. The compound of claim 7 of structural formula Ii:

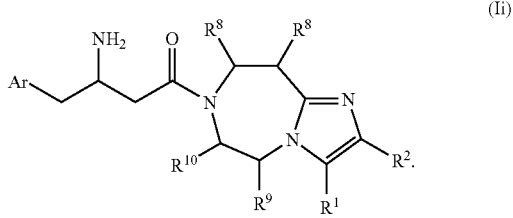

(Ii)

11. The compound of claim 1 wherein $R^3$ is selected from the group consisting of hydrogen, fluoro, chloro, bromo, trifluoromethyl, and methyl.

12. The compound of claim 11 wherein $R^3$ is selected from the group consisting of hydrogen, fluoro, and chloro.

13. The compound of claim 1 wherein $R^1$ is selected from the group consisting of:
  hydrogen,
  halogen,
  $C_{1-6}$ alkyl, wherein alkyl is unsubstituted or substituted with one to five substituents independently selected from halogen or hydroxy,
  $(CH_2)_n$-aryl, wherein aryl is unsubstituted or substituted with one to five substituents independently selected from halogen, CN, hydroxy, $NR^7SO_2R^6$, $SO_2R^6$, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens;
  $(CH_2)_n$-heteroaryl, wherein heteroaryl is unsubstituted or substituted with one to three substituents independently selected from hydroxy, halogen, $C_{1-6}$ alkyl, and $C_{1-6}$ alkoxy, wherein alkyl and alkoxy are unsubstituted or substituted with one to five halogens, and
  wherein any methylene ($CH_2$) carbon atom in $R^1$ is unsubstituted or substituted with one to two groups independently selected from halogen, hydroxy, and $C_{1-4}$ alkyl unsubstituted or substituted with one to five halogens.

14. The compound of claim 13 wherein $R^1$ is selected from the group consisting of
  hydrogen,
  methyl,
  trifluoromethyl,
  phenyl,
  4-fluorophenyl,
  4-(trifluoromethyl)phenyl,
  4-(trifluoromethoxy)phenyl, and
  5-methyl-1,3,4-oxadiazol-2-yl.

15. The compound of claim 1 wherein $R^2$ is selected from the group consisting of
  hydrogen,
  halogen, and
  $C_{1-6}$ alkyl, wherein alkyl is unsubstituted or substituted with one to five substituents independently selected from halogen or hydroxy.

16. The compound of claim 15 wherein $R^2$ is selected from the group consisting of hydrogen and trifluoromethyl.

17. The compound of claim 1 wherein $R^8$, $R^9$, and $R^{10}$ are independently selected from the group consisting of:
  hydrogen and
  $C_{1-6}$ alkyl, unsubstituted or substituted with one to five substituents independently selected from halogen, hydroxy, $C_{1-6}$ alkoxy, and phenyl-$C_{1-3}$ alkoxy, wherein alkoxy is unsubstituted or substituted with one to five halogens.

18. The compound of claim 17 wherein $R^8$, $R^9$, and $R^{10}$ are each independently selected from the group consisting of hydrogen and methyl.

19. The compound of claim 18 wherein $R^9$ and $R^{10}$ are hydrogen.

20. The compound of claim 2 which is selected from the group consisting of:

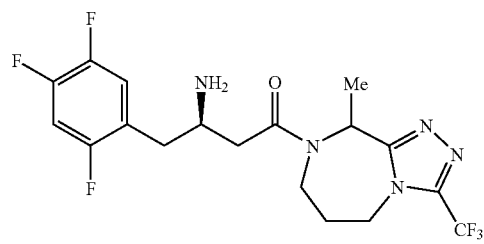

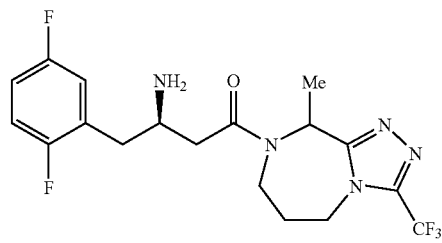

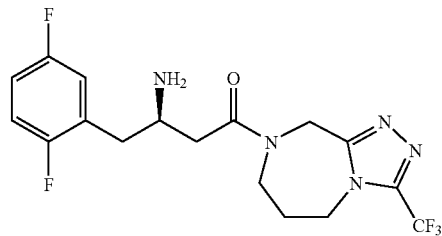

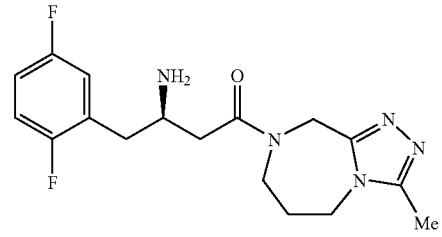

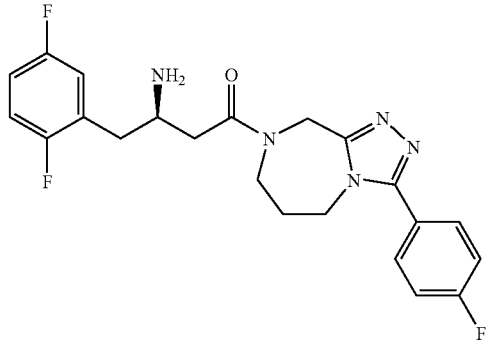

-continued

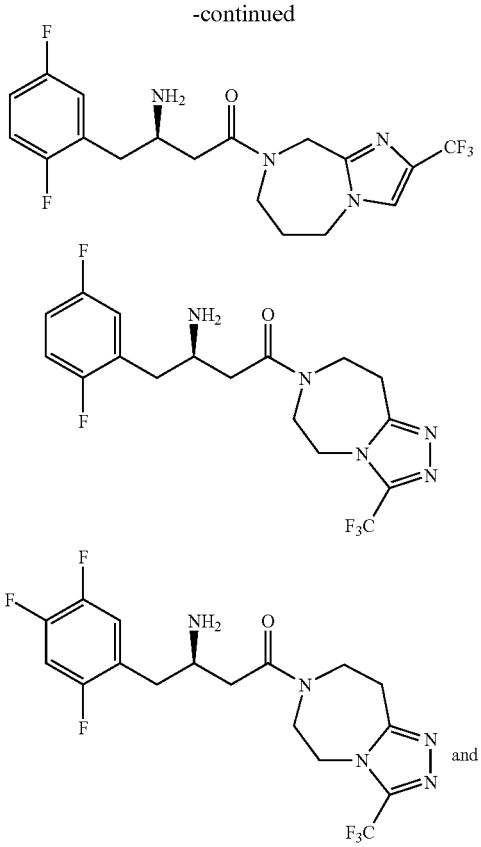

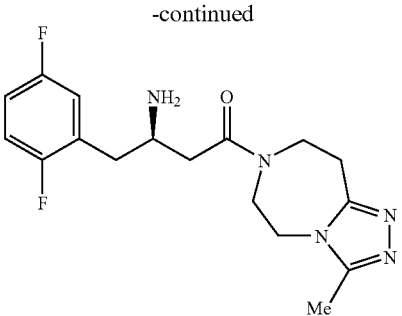

or a pharmaceutically acceptable salt thereof.

21. A pharmaceutical composition which comprises a compound of claim 1 and a pharmaceutically acceptable carrier.

22. A method for treating non-insulin dependent (Type 2) diabetes in a mammal in need thereof which comprises the administration to the mammal of a therapeutically effective amount of a compound of claim 1.

23. A method for treating hyperglycemia in a mammal in need thereof which comprises the administration to the mammal of a therapeutically effective amount of a compound of claim 1.

24. The pharmaceutical composition of claim 21 further comprising a second active ingredient selected from the group consisting of metformin, rosiglitazone, and pioglitazone.

* * * * *